United States Patent
Alonso et al.

(10) Patent No.: US 9,415,077 B2
(45) Date of Patent: Aug. 16, 2016

(54) **EFFECT OF AN ATTENUATED *BORDETELLA* STRAIN AGAINST ALLERGIC DISEASE**

(71) Applicants: Sylvie Claudette Alonso, Singapore (SG); Rui Li, Shanghai (CN); Camille Locht, Lille (FR)

(72) Inventors: Sylvie Claudette Alonso, Singapore (SG); Rui Li, Shanghai (CN); Camille Locht, Lille (FR)

(73) Assignees: Institut National de la Sante et de la Recherche Medicale (FR); Institut Pasteur de Lille (FR); National University of Singapore, Singapore (SG)

( * ) Notice: Subject to any disclaimer, the term of this patent is extended or adjusted under 35 U.S.C. 154(b) by 0 days.

(21) Appl. No.: 14/355,744

(22) PCT Filed: Nov. 2, 2012

(86) PCT No.: PCT/SG2012/000417
§ 371 (c)(1),
(2) Date: May 1, 2014

(87) PCT Pub. No.: WO2013/066272
PCT Pub. Date: May 10, 2013

(65) Prior Publication Data
US 2014/0271563 A1    Sep. 18, 2014

Related U.S. Application Data

(60) Provisional application No. 61/554,798, filed on Nov. 2, 2011.

(51) Int. Cl.
| | |
|---|---|
| *A61K 35/74* | (2015.01) |
| *C12N 1/36* | (2006.01) |
| *C07K 14/235* | (2006.01) |
| *C07K 14/245* | (2006.01) |
| *A61K 39/39* | (2006.01) |
| *A61K 39/00* | (2006.01) |
| *A61K 39/10* | (2006.01) |

(52) U.S. Cl.
CPC ............... *A61K 35/74* (2013.01); *A61K 39/39* (2013.01); *C07K 14/235* (2013.01); *C07K 14/245* (2013.01); *C12N 1/36* (2013.01); *A61K 2039/10* (2013.01); *A61K 2039/522* (2013.01); *A61K 2039/577* (2013.01)

(58) Field of Classification Search
None
See application file for complete search history.

(56) References Cited

U.S. PATENT DOCUMENTS

| | | |
|---|---|---|
| 6,713,072 B1 | 3/2004 | Pizza |
| 6,841,358 B1 | 1/2005 | Locht |
| 2005/0147607 A1 | 7/2005 | Reed |
| 2009/0226490 A1* | 9/2009 | Stanford ............... A61K 39/05 424/234.1 |
| 2009/0246222 A1* | 10/2009 | Locht et al. ............... 424/200.1 |
| 2010/0111996 A1 | 5/2010 | Leclerc |
| 2012/0121647 A1 | 5/2012 | Alonso |
| 2013/0183336 A1 | 7/2013 | Locht |

FOREIGN PATENT DOCUMENTS

| | | |
|---|---|---|
| EP | 2442826 | 4/2012 |
| FR | 2718750 | 10/1995 |
| WO | 9528486 | 10/1995 |
| WO | 9816553 | 4/1998 |
| WO | 03102170 | 12/2003 |
| WO | 2007104451 | 9/2007 |
| WO | 2008156753 | 12/2008 |
| WO | 2010125014 | 11/2010 |
| WO | 2010146414 | 12/2010 |
| WO | 2013066272 | 5/2013 |
| WO | 2014060514 | 4/2014 |

OTHER PUBLICATIONS

Gruber et al. "Common vaccine antigens inhibit allergen-induced sensitization and airway hyperresponsiveness in a murine model", Allergy 61: 820-827, 2006.*

Locht, Camille, et al: "Common accessory genes for the *Bordetella pertussis* filamentous hemagglutinin and fimbriae share sequence similarities with the papC and papD gene families," The EMBO Journal, 1992, vol. 11(9):3175-3183.

Locht, Camille et al: "Bordetalla pertussis, molecular pathogenesis under multiple aspects," Current Opinion in Microbiology, 2001, vol. 4:82-89.

Kashimoto, Takashige, et al: "Identification of functional domains of Bordetella dermonecrotizing toxin," Infect. Immun., 1999, vol. 67(8):3727-3732.

Kavanagh, H. et al: "Attenuated bordetella pertussis vaccine strain BPZE1 modulates allergen-induced immunity and prevents allergic pulmonary pathology in a murine model," Clinical & Experimental Allergy, 2010, vol. 40(933-941.

Ho, Si Ying et al: "Highly attenuated Bordetella pertussis Strain BPZE1 as a potential live vehicle for delivery of heterologous vaccine candidates," Infection and Immunity, 2008, vol. 76:111-119.

Higgins, Sarah C. et al: "Toll-like receptor 4-mediated innate IL-10 activates antigen-specific regulatory T cells and confers resistance to Bordetella pertussis by inhibiting inflammatory pathology," The Journal of Immunology, 2003, vol. 171:3119-3127.

Feunou, Pascal et al: "Genetic stability of the live attenuated Bordetella pertussis vaccine candidate BPZE1," Vaccine, 2008, vol. 28:5722-5727.

Ennis, D.P. et al: "Prior Bordetella pertussis infection modulates allergen priming and the severity of airway pathology in a murine model of allergic asthma," Clin Exp Allergy, 2004, vol. 34:1488-1497.

(Continued)

Primary Examiner — Emily Cordas
(74) Attorney, Agent, or Firm — Stanley A. Kim

(57) ABSTRACT

Described herein are compositions, vaccines, and methods that include use of a mutated *Bordetella* strain against allergic diseases such as asthma and skin inflammation. Also described are kits. Other compositions, vaccines, and methods are also described.

8 Claims, 6 Drawing Sheets

(56) References Cited

OTHER PUBLICATIONS

Ennis, D.P. et al: Whole-cell pertussis vaccine protects against Bordetella pertussis exacerbation of allergic asthma, Immunology Letters 97, 2005, pp. 91-100.

Das, Pam: "Whopping cough makes global comeback," The Lancet Infectious Diseases, 2002, vol. 2:322.

Coppens, Isabelle et al: "Production of Neisseria meningitidis transferrin-binding protein B by recombinant Bordetella pertussis," Infection and Immunity, 2001, pp: 5440-5446.
Child Innovac; European Network on Nasal Vaccination against Respiratory Infections in Young Children, 2008, http://www.ist-world.org/ProjectDetails.aspx?; last accessed on Jan. 6, 2015.
Carbonetti, Nicholas H.: "Immunomodulation in the pathogenesis of Bordetella pertussis infection and disease," Current Opinion in Pharmacology, 2007, vol. 7:272-278.
Antoine, R. and C. Locht: "Roles of the disulfide bond and the carboxy-terminal region of the S1 subunit in the assembly and biosynthesis of pertussis toxin," Infect.Immun., 1990, vol. 56(6):1518-1526.
Alonso, Sylvie et al: "Production of nontypeable haemophilus influenzae HtrA by recombinant Bordetella pertussis with the use of filamentous hemagglutinin as a carrier," Infection and Immunity, 2005, pp. 4295-4301.
Abe, Takayuki et al: "Baculovirus induces an innate immune response and confers protection from lethal influenza virus infection in mice," J Immunol, 2003, vol. 171:1133-1139.
Feunou, Pascal et al: "Long-term immunity against pertussis induced by a single nasal administration of live attenuated B. pertussis BPZE1," Vaccine, 2010, vol. 28:7047-7053.
Mielcarek, Nathalie et al: "Dose Response of attenuated Bordetella pertussis BPZE1-induced protection in mice," Clinical and Vaccine Immunology, 2010, pp. 317-324.
Mielcarek, Nathalie et al: "Live attenuated B. pertussis as a single-dose nasal vaccine against whooping cough," PLoS Pathogens, 2006, vol. 2(7): 662-670.
Renauld-Mongenie, G. et al:Distinct roles of the N-terminal and C-terminal precursor domains in the biogenesis of the Bordetella pertussis filamentous hemagglutinin, J. Bacteriol., 1996, vol. 178(4):1053-1060.
Mattoo, S. et al: "Mechanisms of Bordetella pathogenesis," Frontiers in Bioscience, 2001, vol. 6:168-186.
Mattoo, S. and James D. Cherry: "Molecular pathogenesis, epidemiology, and clinical manifestations of respiratory infections due to Bordetella pertussis and other *Bordetella* subspecies," Clinical Microbiology Reviews, 2005, vol. 18(2):326-382.
Martignon, G. et al: "Does childhood immunization against infectious diseases protect from the development of atopic disease," Pediatr Allergy Immunol, 2005, vol. 16:193-200.
Locht, Camille et al: "Bordetella pertussis: from functional genomics to intranasal vaccination," Int. J. Med. Microbiol., 2004, vol. 293:583-588.
Harju, T.H. et al: Pathogenic bacteria and viruses in induced sputum or pharyngeal secretions of adults with stable asthma, Thorax, 2006, vol. 61:579-584.
Grueber, C. et al: "Early atopic disease and early childhood immunization—is there a link?," Allergy, 2008, vol. 63:1464-1472.
Gern, James E.: "Viral and bacterial infections in the development and progression of asthma," J Allergy Clin Immunol, 2000, pp: S497-S501.
Ennis, Darren P.: "Acellular pertussis vaccine protects against exacerbation of allergig asthma due to Bordetella pertussis in a murine model," Clin. Diagn. Lab. Immunol., 2005, vol. 12(3):409-417.
Kim, Young-Suk, et al.: "Inhibition of murine allergic airway disease by Bordetella pertussis," Immunology, 2004, vol. 112:624-630.
Yusibov, V. et al.: "Peptide-based candidate vaccine against respiratory syncytial virus," Vaccine, 2005, vol. 23:2261-2265.
Walker, K. E. et al: "Characterizationof the dermonecrotic toxin in members of the genus *Bordetella*," Infect. Immun., 1994, vol. 62, No. 9:3817-3828.
Teman, UA. et al.: "A novel role for murine IL-4 in vivo: induction of MUC5AC gene expression and mucin hypersecretion," Am J Respir Cell Mol Biol., 1997, vol. 16(4):471-478.
Stith, Rebecca et al.: "The link between tracheal cytotoxin production and peptidoglycan recycling in Bordetella Pertussis," Abstracts of the General Meeting of the American Society for Microbiology, New Orleans; 1996; vol. 96:184 (XP008013937).
Li, Rui, et. al.: "Attenuated Bordetella pertussis BPZE1 as a live vehicle for heterologous vaccine antigens delivery thorugh the nasal route," Bioengineered Bugs, 2011, vol. 2(6):315-319.
Li, Rui, et al.: "Development of live attenuated Bordetella pertussis strains expressing the universal influenza vaccine candidate M2e," Vaccine, 2011, vol. 29:L5502-5511.
Romagnani, Sergio, "Immunologic influences on allergy and the TH1/TH2 balance," J Allergy Clin Immunol, 2004, pp. 395-400.
Nemery, B. et al.: "Interstitial lung disease induced by exogenous agents: factors governing susceptibility," Eur Respir J, 2001, vol. 18, Suppl. 32:30s-42s.
Neirynck, Sabine, et al.: "A universal influenza A vaccine based on the extracellular domain of the M2 protein," Nature Medicine, 1999, vol. 5:1157-1163.
Nagel, Gabriele et al.: "Association of pertussis and measles infections and immunizations with asthma and allergic sensitization in ISAAC Phase Two," Pediatric Allergy and Immunology, 2012, vol. 23:736-745.
Morokata, T. et al.: "C57BL/6 mice are more susceptible to antigen-induced pulmonary eosinophilia than BALB/c mice, irrespective of systemic T helper 1/T helper 2 responses," Immunology, 1999, vol. 98:345-351.
Mielcarek, Nathalie et al.: "Homologous and heterologous protection after single intranasal administration of live attenuated recombinant Bordetella pertussis," Nature Biotechnology, 1998, vol. 16:454-457.
Marsland, B.J., et al.: "Allergic airway inflammation is exacerbated during acute influenza infection and correlates with increased allergen presentation and recruitment of allergen-specific T-helper type 2 cells," Clinical & Experimental Allergy, 2004, vol. 34, Issue 8.
Mahon, B., et al.: "Atypical Disease after Bordetella pertussis Respiratory Infection of Mice with Targeted Disruptions of Interferon-γ Receptor or Immunoglobulin μ Chain Genes," J. Exp. Med., 1997, vol. 186, No. 11:1843-1851.
Locht, Camille, et al.: "Bordetella pertussis: from functional genomics to intranasal vaccination," Iny. J. Med. Microbiol., 2004, vol. 293:583-588.
Li, Z.M., et al.: "Cloning and sequencing of the structural gene for the porin protein of Bordetella pertussis," Molecular Biology, 1991, vol. 5 (7):1649-1656.
De Filette et al.: "Improved design and intranasal delivery of an M2e-based human influenza A vaccine," Vaccine, 2006, vol. 24, pp. 6597-6691.
Laemmli, U.K.: "Cleavage of Structural Proteins during the Assembly of the Head of Bacteriophage T4," Nature, 1970, pp. 680-685.
Humbert, Marc et al.: "Elevated expression of messenger ribonucleic acid encoding IL-13 in the bronchial mucosa of atopic and nonatopic subjects with asthma," Journal of Allergy and Clinical Immunology, 1997, vol. 99 (5):657-665.
Holgate, Stephen, et al.: "The anti-inflammatory effects of omalizumab confirm the central role of IgE in allergic inflammation," J Allergy Clin Immunol, 2005, vol. 115:459-465.
Hausman, Sally Z. and Burns, Drusilla L.: "Use of Pertussis Toxin Encoded by ptx Genes from *Bordetella bronchiseptica* to Model the Effects of Antigenic Drift of Pertussis Toxin on Antibody Neutralization,".
Hansen, Gesine et al.: "Allergen-specific Th1 cells fail to counterbalance Th2 cell-induced airway hyperreactivity but cause severe airway inflammation," J. Clin. Invest., 1999, vol. 103:175-183.
Hamelmann, E. et al.: "Role of IgE in the development of allergic airway inflammation and airway hyperresponsiveness a murine model," Allergy, 1999, vol. 54:297-305, abstract only.
Gleich, Gerald J.: "Mechanisms of eosinophil-associated inflammation," J. Allergy Clin. Immunol., 2000, pp. 651-663.

(56) References Cited

OTHER PUBLICATIONS

Giefing, Carmen et al.: "Discovery of a novel class of highly conserved vaccine antigens using genomic scale antigenic fingerprinting of pneumococcus with human antibodies," JEM, 2008, vol. 205(1):117-131.
Galli, Stephen J., et al.: "The development of allergic inflammation," Nature, 2008, vol. 454:445-454.
Zhao, Zhanqin, et al.: "Protecting mice from fatal Bordetella brochiseptica infection by immunization with recombinant pertactin antigens," Acta Microbiologica Sinica, 2008, vol. 48 (3):337-341.
Willems, Rob J.L. et al: "The efficacy of a whole cell pertussis vaccine and fimbriae against Bordetella pertussis and Bordetella parapertussis infections in a respiratory mouse model," Vaccine, 1998, vol. 16 (4)410-416.
Varga, Steven M. et al: "The Attachment (G) Glycoprotein of Respiratory Syncytial Virus Contains a Single Immunodominant Epitope That Elicits Both Th1 and Th2 CD4+ T Responses," The Journal of Immunology, 2000, vol. 165:6487-6495.
Stibitz, Scott: "Use of conditionally counterselectable suicide vectors for allelic exchange," Methods in Enzymology, 1994, vol. 235:458-465; Abstract.
Stainer, D.W. and M.J. Scholte: "A simple chemically defined medium for the production of phase I Bordetella pertussis," Journal of General Microbiology, 1971, vol. 63:211-220.
Skerry, Ciaran M. and Bernard P. Mahon: "A live, attenuated bordetella pertussis vaccine provides long-term protection against virulent challenge in a murine model," Clinical and Vaccine Immunology, 2011, vol. 18:187-193.
Simon, R. et al: "A broad host range mobilization system for in vivo genetic engineering: transposon mutagenesis in gram negative bacteria," Nature Biotechnology, 1983, vol. 1:784-791.
Reveneau, Nathalie et al: "Tetanus toxin fragment C-specific priming by intranasal infection with recombinant Bordetella pertussis," Vaccine, 2002, vol. 20:926-933.
Renauld-Mongenie, Genevieve, et al: "Induction of mucosal immune responses against a heterologous antigen fused to filamentous hemagglutinin after intranasal immunization with recombinant Bordetella pertussis," Proc. Natl. Acad. Sci., 1996, vol. 93:7944-7949.
Quandt, J. and Michael F. Hynes: "Versatile suicide vectors which allow direct selection for gene replacement in gram-negative bacteria," Gene, 1993, vol. 127 (1):15-21; Abstract.
Power, Ultan F. et al: "Identification and characterisation of multiple linear B cell protectopes in the respiratory syncytial virus G protein," Vaccine, 2001, vol. 19, Issues 17-19:2345-2351; Abstract.
Feunou, Pascal: "T.119.T—but not B-cell-mediated protection induced by nasal administration using live attenuated bordetella pertussis BPZE1 Cross Protect Against B. Parapertussis," Clinical Immunology, 2009, vol. 131, Supplement 1, p. S86; Abstract.
Narasaraju, T. et al: "Adaptation of human influenza H3N2 virus in a mouse peumonitis model: insights into viral virulence, tissue tropism and host pathogenesis," Microbes and Infection 11, 2009:2-11.
Mutsch, M. et al: Use of the inactivated intranasal influenza vaccine and the risk of Bell's Palsy in Switzerland, The New England Journal of Medicine, 2004, vol. 350:896-903.
Mills, KH et al: "A respiratory challenge model for infection with Bordetella pertussis application in the assessment of pertussis vaccine potency and in defining the mechanism of protective immunity," Dev Biol Stand, 1998, vol. 95:31-41; Abstract.
Mielcarek, Nathalie et al: "Attenuated bordetella pertussis: new live vaccines for intranasal immunisation," Vaccine, 2006, S2:54-55.
Mielcarek, Nathalie et al: "Intranasal priming with recombinant Bordetella pertussis for the induction of a systemic immune response against a heterologous antigen," Infection and Immunity, 1997:544-550.
Mielcarek, Nathalie et al: "Nasal vaccination using live bacterial vectors," Advanced Drug Delivery Review, 2001, vol. 51:55-69.
Mekseepralard, C. et al: "Protection of mice against human respiratory syncytial virus by wild-type and aglycosyl mouse-human chimaeric IgG antibodies to subgroup-conserved epitopes on the G glycoprotein," Journal of General Virology, 2006, vol. 87:1267-1273.
Menozzi, F.D. et al: "Identification and purification of transferring- and lactoferrin-binding proteins of bordetella pertussis and bordetella bronchiseptica," Infection and Immunity, 1991:3982-3988.
McGuirk, P. et al: Pathogen-specific T regulatory 1 cells induced in the respiratory tract by a bacterial molecule that stimulates interleukin 10 production by dendritic cells: a novel strategy for evasion of protective T helper type 1 resonses by Bordella pertussis.
Mascart, Francoise, et al: "Bordetella pertussis infection in 2-month-old infants promotes type 1 T cell responses," The Journal of Immunology, 2003, vol. 170:1504-1509.
Marsolais, David et al: "A critical role for the sphingosine analog AAL-R in dampening the cytokin response during Infuenza virus infection," The National Academy of Sciences of the USA, 2009, vol. 106(5):1560-1565.

* cited by examiner

EFFECT OF AN ATTENUATED *BORDETELLA* STRAIN AGAINST ALLERGIC DISEASE

CROSS REFERENCE TO RELATED APPLICATIONS

The present application is the U.S. national phase under 35 U.S.C. 371 of international application number PCT/SG2012/000417, filed Nov. 2, 2012, which designated the U.S. and claims the priority of U.S. Provisional Application No. 61/554,798, filed Nov. 2, 2011, all of which are incorporated herein by reference in their entirety.

FIELD

The various aspects disclosed herein relate to fields of microbiology, immunology, and virology.

BACKGROUND

It has been previously reported that prior nasal administration of the highly attenuated strain of *Bordetella pertussis*, BPZE1, provides effective and sustained protection against lethal challenge with influenza A viruses at least by suppressing the production of major pro-inflammatory mediators [1 and PCT/US2009/047399].

Asthma is a chronic inflammatory lung disease characterized by intermittent airflow obstruction, airway hyperreactivity (AHR), mucus hypersecretion, enhanced IgE responses and infiltration of inflammatory cells—mainly eosinophils into the airways (2). In recent years, the incidence of asthma has increased dramatically, with the greatest prevalence observed in developed countries (3). Although altered Th2/Th1 balance with a Th2-dominant immune response has been shown to be important in the development of asthma, the mechanism underlying the pathogenesis of asthma remains to be fully deciphered (4).

Allergic contact dermatitis (ACD) caused by reactive haptens and metal ions is a form of delayed type hypersensitivity, and is one of the most common skin diseases worldwide (5). Contact hypersensitivity (CHS) is a recognized mouse model for studying human ACD and is an epidermal T cell-mediated inflammatory response to low molecular weight haptens (6,7).

According to the hygiene hypothesis, frequent exposure to pathogens triggers a certain degree of protective immunity against atopic diseases (8). However, conflicting observations have been reported regarding the protective versus detrimental role of the pre-exposure to viral or bacterial microorganisms against allergic diseases (9-13), underscoring that the effect of encounter with pathogenic and nonpathogenic bacteria on shaping the host immune response is complex and remains poorly understood. Furthermore, despite intensive studies on the mechanisms and optimal medical management, current therapeutic approaches that tackle these inflammatory disorders are largely ameliorative rather than curative and can cause unexpected side effects (14). In addition many asthmatic patients develop resistance to treatment and/or progressive pulmonary dysfunction (14). Thus there remains an ongoing need for better therapies to treat allergic diseases, such as those described herein.

SUMMARY

Described herein is a method of eliciting an immune response capable of reducing the severity an allergic disease in a mammal in need thereof, comprising: administering a mutated *Bordetella* strain to the mammal, wherein the strain comprises a mutated pertussis toxin (ptx) gene, a deleted or mutated dermonecrotic (dnt) gene, and a heterologous ampG gene, and wherein the administration elicits the immune response.

In some aspects, the *Bordetella* strain is a *Bordetella pertussis* strain. In some aspects, the wild-type *Bordetella* strain ampG gene is replaced by an *E. coli* ampG gene. In some aspects, the mutation of the ptx gene comprises the substitution of an amino acid involved in substrate binding and/or an amino acid involved in catalysis. In some aspects, the substitution of the amino acid involved in substrate binding comprises R9K and the substitution of the amino acid involved in catalysis comprises E129G. In some aspects, the *Bordetella* strain is a triple mutant strain. In some aspects, the *Bordetella* strain is a BPZE1 strain. In some aspects, the *Bordetella* strain is attenuated. In some aspects, the *Bordetella* strain is a live strain. In some aspects, the heterologous ampG gene is the only heterologous gene in the strain. In some aspects, the *Bordetella* strain does not comprise a heterologous expression platform to carry heterologous antigens to the respiratory mucosa of the mammal.

In some aspects, the method further includes preventing or treating the allergic disease. In some aspects, the *Bordetella* strain is administered prior to onset of the allergic disease in the mammal. In some aspects, the *Bordetella* strain is administered about 6 weeks or more prior to onset of the allergic disease in the mammal. In some aspects, the *Bordetella* strain is administered about 2 weeks or more prior to onset of the allergic disease in the mammal. In some aspects, the allergic disease is asthma. In some aspects, the allergic disease is skin inflammation. In some aspects, the allergic disease is allergic contact dermatitis (ACD). In some aspects, the immune response comprises a Th2 immune response. In some aspects, the immune response comprises a Th1 immune response. In some aspects, the strain is administered to the mammal by subcutaneous (s.c.), intradermal (i.d.), intramuscular (i.m.), intravenous (i.v.), oral, or intranasal (i.n.) administration; or by injection or by inhalation. In some aspects, the strain is administered intranasally. In some aspects, the strain is administrated to a mammal in need of protective immunity against the allergic disease.

In some aspects, the mammal is at risk of developing the allergic disease.

In some aspects, the strain is administered in a single dose. In some aspects, the strain is administered in more than one dose. In some aspects, the strain is administered in two doses. In some aspects, the two doses are administered about 3 weeks apart. In some aspects, a level of protection against the allergic disease is greater than about 60%. In some aspects, a level of protection against the allergic disease is greater than about 50%.

In some aspects, the mammal is a human. In some aspects, the mammal is a child.

Also described herein is a method of eliciting a protective immune response against an allergic disease in a human at risk of developing the allergic disease, comprising: intranasally administering a live and attenuated BPZE1 strain to the human prior to onset of the allergic disease in the human, wherein administration elicits the immune response.

Also described herein is a method of eliciting an immune response against an allergic disease in a human in need thereof, comprising: administering a live, mutated *Bordetella* strain to the human, wherein administration elicits the immune response.

Also described herein is a method of protecting a mammal against an allergic disease, comprising: administering to the mammal a mutated *Bordetella* strain comprising a mutated ptx gene, a deleted or mutated dnt gene, and a heterologous ampG gene, wherein the mammal is protected against the allergic disease.

Also described herein is a method of providing a protective form of immunity against an allergic disease in a mammal in need thereof, comprising: administering to the mammal a mutated *Bordetella* strain comprising a mutated ptx gene, a deleted or mutated dnt gene, and a heterologous ampG gene, wherein the mammal is provided with the protective form of immunity.

Also described herein is a composition formulated for use in treating or preventing an allergic disease in a mammal in need thereof, comprising: a mutated *Bordetella* strain, wherein the strain comprises a mutated pertussis toxin (ptx) gene, a deleted or mutated dermonecrotic (dnt) gene, and a heterologous ampG gene.

In some aspects, the *Bordetella* strain is a *Bordetella pertussis* strain. In some aspects, the wild-type *Bordetella* strain ampG gene is replaced by an *E. coli* ampG' gene. In some aspects, the mutation of the ptx gene comprises the substitution of an amino acid involved in substrate binding and/or an amino acid involved in catalysis. In some aspects, the substitution of the amino acid involved in substrate binding comprises R9K and the substitution of the amino acid involved in catalysis comprises E129G. In some aspects, the *Bordetella* strain comprises a triple mutant strain. In some aspects, the *Bordetella* strain is a BPZE1 strain. In some aspects, the *Bordetella* strain is attenuated. In some aspects, the *Bordetella* strain is a live strain. In some aspects, the *Bordetella* strain does not comprise a heterologous gene other than the heterologous ampG gene. In some aspects, the *Bordetella* strain does not comprise a heterologous expression platform to carry heterologous antigens to the respiratory mucosa of the mammal.

In some aspects, the composition further includes a pharmaceutically suitable excipient, vehicle, and/or carrier. In some aspects, the composition further includes an adjuvant. In some aspects, the composition further includes a small molecule capable of affecting the allergic disease.

Also described herein is a composition formulated for use in treating or preventing an allergic disease in a mammal in need thereof comprising a *Bordetella* strain identified by accession number CNCM I-3585.

Also described herein is a composition formulated for use in treating or preventing an allergic disease in a mammal in need thereof comprising a *Bordetella* strain identified by accession number V09/009169.

Also described herein is a vaccine comprising a composition described herein for treating or preventing the allergic disease in the mammal. In some aspects, the vaccine is formulated for intranasal administration.

BRIEF DESCRIPTION OF THE DRAWINGS

These and other features, aspects, and advantages will become better understood with regard to the following description, and accompanying drawings, where.

DETAILED DESCRIPTION

Figure 1:
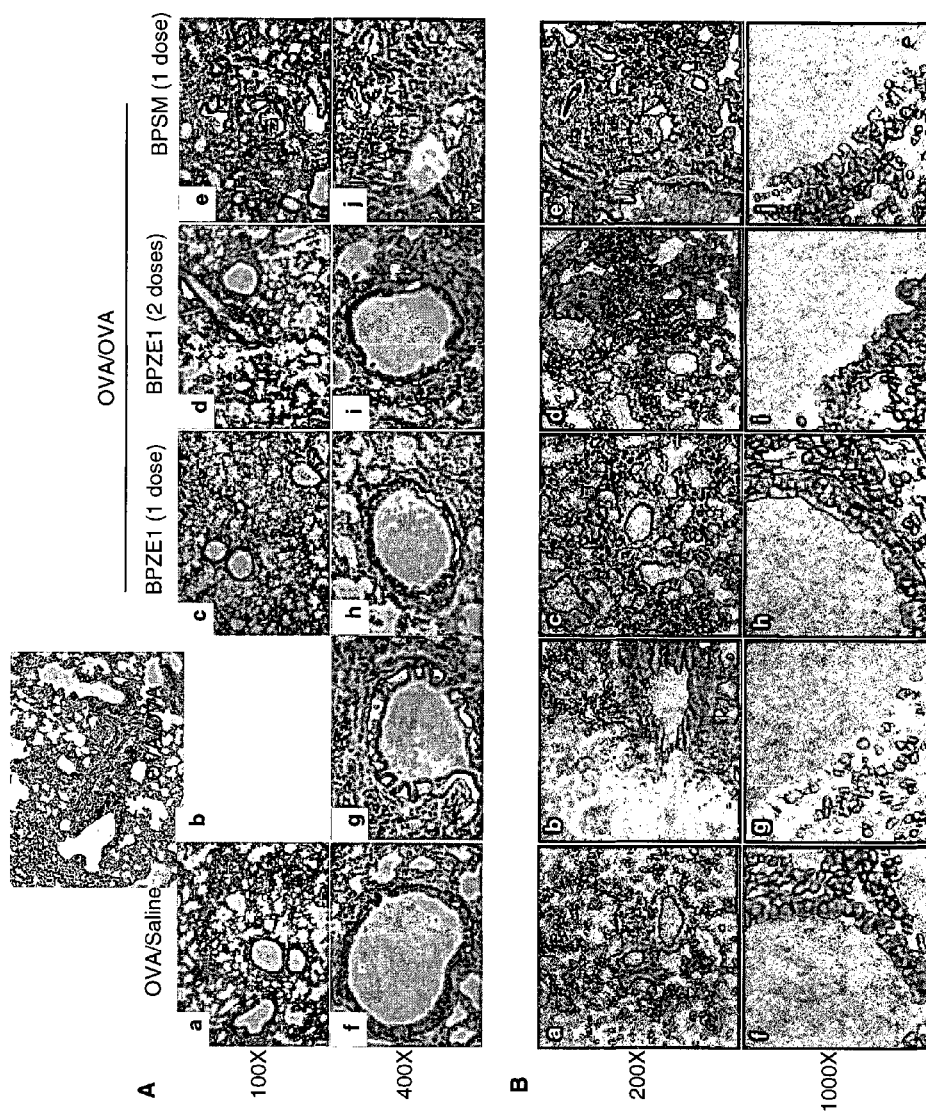
FIG. 1. Effects of BPZE1 pre-treatment on OVA-induced airway pathology. Airway inflammation was analyzed by hematoxylin and eosin staining (A) and periodic acid-fluorescence Schiff stain (PAFS) (B). Representative morphological changes of fixed lung sections from OVA/Saline (a and f), OVA/OVA (b and g), BPZE1 (1 dose)+OVA/OVA (c and h), BPZE1 (2 doses)+OVA/OVA (d and i) and BPSM (1 dose)+OVA/OVA (e and j) were viewed under 100× (panel A a-e) and 400× (panel A f-j) magnification for H&E staining, 200× (panel B a-e) and 1000× (panel B f-j) magnification for PAFS.

Terms used in the claims and specification are defined as set forth below unless otherwise specified.

The term "attenuated" refers to a weakened, less virulent *Bordetella* strain that is capable of stimulating an immune response and creating protective immunity, but does not generally cause illness.

The term "rapid protective immunity" means that immunity against *Bordetella* is conferred in a short time after administration of a mutated *Bordetella* strain.

The term "*Bordetella* strain" includes strains from *Bordetella pertussis, Bordetella parapertussis*, and *Bordetella bronchiseptica.*

As used herein, the abbreviation "PTX" refers to pertussis toxin, which synthesizes and secretes an ADP-ribosylating toxin. PTX is comprised of five different subunits (named S1-S5) with each complex containing two copies of S4. The subunits are arranged in an A-B structure. The A component is enzymatically active and is formed from the S1 subunit, while the B component is the receptor binding portion and is made up of subunits S2-S5.

As used herein the abbreviation "DNT" refers to pertussis dermonecrotic toxin, which is a heat labile toxin that can induce localized lesions in mice and other laboratory animals when it is injected intradermally.

As used herein the abbreviation "TCT" refers to tracheal cytotoxin, which is a virulence factor synthesized by Bordetellae. TCT is a peptidoglycan fragment and has the ability to induce interleukin-1 production and nitric oxide synthase. It has the ability to cause stasis of cilia and has lethal effects on respiratory epithelial cells.

As used herein the abbreviation "ampG" refers to a gene that codes for a permease for the transport of 1,6-GlcNac-anhydro-MurNAc.

The term "mammal" as used herein includes both humans and non-humans and include but is not limited to humans, non-human primates, canines, felines, murines, bovines, equines, and porcines. Mammals can include mammals that are pre-birth or post-birth.

The term "child" is meant to be a mammal (e.g., a human) between 0 months (birth) and less than or equal to 18 years of age.

"Treating" refers to any indicia of success in the treatment or amelioration or prevention of the disease, condition, or disorder, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents to prevent or delay, to alleviate, or to arrest or inhibit development of the symptoms or conditions associated with a disease, condition or disorder as described herein. The term "therapeutic effect" refers to the reduction, elimination, or prevention of the disease, symptoms of the disease, or side effects of the disease in the subject. "Treating" or "treatment" using the methods disclosed herein includes preventing the onset of symptoms in a subject that can be at increased risk of a disease or disorder associated with a disease, condition or disorder as described herein, but does not yet experience or exhibit symptoms, inhibiting the symptoms of a disease or disorder (slowing or arresting its development), providing relief from the symptoms or side effects of a disease (including palliative treatment), and relieving the symptoms of a disease (causing regression). Treatment can be prophylactic (to prevent or delay the onset of the disease, or to prevent the manifestation of clinical or subclinical symptoms thereof) or therapeutic suppression or alleviation of symptoms after the manifestation of the disease or condition.

"Concomitant administration" of a known drug (or other compound) with a composition disclosed herein means administration of the drug (or other compound) together with the composition at such time that both the known drug (or other compound) will have a therapeutic effect or diagnostic effect. Such concomitant administration can involve concurrent (i.e., at the same time), prior, or subsequent administration of the drug (or other compound) with respect to the administration of a composition. A person of ordinary skill in the art would have no difficulty determining the appropriate timing, sequence, and dosages of administration for particular drugs (or other compounds) together with a composition.

The terms "protection" and "prevention" are used herein interchangeably and mean that a disease, condition, or disorder is impeded.

"Prophylaxis vaccine" means that this vaccine prevents a disease, condition, or disorder.

The term "immunogenic composition" or "composition" means that the composition can induce an immune response and is therefore antigenic. By "immune response" means any reaction by the immune system. These reactions include the alteration in the activity of an organism's immune system in response to an antigen and can involve, for example, antibody production, induction of cell-mediated immunity, complement activation, or development of immunological tolerance.

As used herein, the term "disease" has the meaning generally known and understood in the art and comprises any abnormal condition in the function or well being of a host individual. A diagnosis of a particular disease by a healthcare professional can be made by direct examination and/or consideration of results of one or more diagnostic tests.

The term "allergic disease" refers to a hypersensitivity disorder of the immune system that is characterized by the activation of immune cells that results in the release of inflammatory substances, such as histamine, and the production of IgE antibodies. In some aspects, an allergic disease can be a pathological condition in which a subject is hypersensitized to and can mount an abnormal immunologic reaction against a substance. An allergic disease can be characterized by activation of mast cells by IgE resulting in an inflammatory response (e.g. local response, systemic response) that can result in symptoms as benign as a runny nose, to life-threatening anaphylactic shock and death. Examples of allergic disease include, but are not limited to, allergic rhinitis (e.g., hay fever), asthma (e.g., allergic asthma), skin inflammation, allergic dermatitis (e.g., eczema), contact dermatitis, allergic contact dermatitis (ACD), food allergy, and urticaria (hives).

The terms "live vaccine composition", "live vaccine", "live bacterial vaccine", and similar terms refer to a composition comprising a strain of live *Bordetella* bacteria that provides at least partial protective immunity against a disease, condition, or disorder.

The terms "oral", "enteral", "enterally", "orally", "non-parenteral", "non-parenterally", and the like, refer to administration of a compound or composition to an individual by a route or mode along the alimentary canal. Examples of "oral" routes of administration of a composition include, without limitation, swallowing liquid or solid forms of a vaccine composition from the mouth, administration of a vaccine composition through a nasojejunal or gastrostomy tube, intraduodenal administration of a vaccine composition, and rectal administration, e.g., using suppositories that release a live bacterial vaccine strain described herein.

The term "topical administration" refers to the application of a pharmaceutical agent to the external surface of the skin or the mucous membranes (including the surface membranes of the nose, lungs and mouth), such that the agent crosses the external surface of the skin or mucous membrane and enters the underlying tissues. Topical administration can result in a limited distribution of the agent to the skin and surrounding tissues or, when the agent is removed from the treatment area by the bloodstream, systemic distribution of the agent. In one form, the agent is delivered by transdermal delivery, e.g., using a transdermal patch. Transdermal delivery refers to the diffusion of an agent across the skin (stratum corneum and epidermis), which acts as a barrier few agents are able to penetrate. In contrast, the dermis is permeable to absorption of many solutes and drugs, and topical administration therefor occurs more readily through skin which is abraded or otherwise stripped of the epidermis to expose the dermis. Absorption through intact skin can be enhanced by combining the active agent with an oily vehicle (e.g., creams, emollients, penetration enhancers, and the like, as described, e.g., in Remington's Pharmaceutical Sciences, current edition, Gennaro et al., eds.) prior to application to the skin (a process known as inunction).

The term "nasal administration" refers to any form of administration whereby an active ingredient is propelled or otherwise introduced into the nasal passages of a subject so that it contacts the respiratory epithelium of the nasal cavity, from which it is absorbed into the systemic circulation. Nasal administration can also involve contacting the olfactory epithelium, which is located at the top of the nasal cavity between the central nasal septum and the lateral wall of each main nasal passage. The region of the nasal cavity immediately surrounding the olfactory epithelium is free of airflow. Thus, specialized methods must typically be employed to achieve significant absorption across the olfactory epithelium.

The term "aerosol" is used in its conventional sense as referring to very fine liquid or solid particles carried by a propellant gas under pressure to a site of therapeutic application. A pharmaceutical aerosol can contain a therapeutically active compound, which can be dissolved, suspended, or emulsified in a mixture of a fluid carrier and a propellant. The aerosol can be in the form of a solution, suspension, emulsion, powder, or semi-solid preparation. Aerosols are intended for administration as fine, solid particles or as liquid mists via the respiratory tract of a patient. Various types of propellants can be utilized including, but not limited to, hydrocarbons or other suitable gases. Aerosols can also be delivered with a nebulizer, which generates very fine liquid particles of substantially uniform size within a gas. A liquid containing the active compound is dispersed as droplets, which can be carried by a current of air out of the nebulizer and into the respiratory tract of the patient.

The term "ameliorating" refers to any therapeutically beneficial result in the treatment of a disease state, e.g., an allergic disease state, including prophylaxis, lessening in the severity or progression, remission, or cure thereof.

In general, the phrase "well tolerated" refers to the absence of adverse changes in health status that occur as a result of the treatment and would affect treatment decisions.

"Synergistic interaction" refers to an interaction in which the combined effect of two or more agents is greater than the algebraic sum of their individual effects.

The term "in vitro" refers to processes that occur in a living cell growing separate from a living organism, e.g., growing in tissue culture.

The term "in vivo" refers to processes that occur in a living organism.

The term "sufficient amount" means an amount sufficient to produce a desired effect, e.g., an amount sufficient to cause protein aggregation in a cell.

The term "therapeutically effective amount" is an amount that is effective to ameliorate a symptom of a disease. A therapeutically effective amount can be a "prophylactically effective amount" as prophylaxis can be considered therapy.

It is to be understood that the various aspects of the invention are not limited to particular methods, reagents, compounds, compositions, kits, or biological systems, which can, of course, vary. It is also to be understood that the terminology used herein is for the purpose of describing particular aspects only, and is not intended to be limiting.

As used in this specification and the appended claims, the singular forms "a", "an", and "the" include plural referents unless the content clearly dictates otherwise. Thus, for example, reference to "a vaccine" includes a combination of two or more vaccines, and the like.

Compositions

*Bordetella* Strains

Provided herein is a mutated *Bordetella* strain that can be used as an immunogenic composition or a vaccine to elicit an immune response in a mammal. In one aspect, the mutated *Bordetella* strain contains a mutated ptx gene, a deleted or mutated dnt gene, and a heterologous ampG gene. The heterologous ampG gene product can reduce in large quantities the amount of tracheal cytotoxin that is produced. In one aspect, the strain is BPZE1. The starting strain which is mutated can be any *Bordetella* strain including *Bordetella pertussis*, *Bordetella parapertussis*, and *Bordetella bronchiseptica*. In one aspect the starting strain used to obtain the mutated *Bordetella* strain is *B. pertussis*. In another aspect, the strain is a triple mutant *Bordetella* strain. In another aspect, the *Bordetella* strain is identified by accession number CNCM I-3585. In another aspect, the *Bordetella* strain is identified by accession number V09/009169.

The strains that can be used are not limited to only the mutants described above. Other additional mutations can be undertaken such as adenylate cyclase (AC) deficient mutants, lipopolysaccharide (LPS) deficient mutants, filamentous hemagglutinin (FHA), and any of the bvg-regulated components.

The construction of a mutated *Bordetella* strain can begin with replacing the *Bordetella* ampG gene in the strain with a heterologous ampG gene. Any heterologous ampG gene known in the art can be used. Examples of these can include all gram-negative bacteria that release very small amounts of peptidoglycan fragments into the medium per generation. Examples of gram-negative bacteria include, but are not limited to: *Escherichia coli*, *Salmonella*, Enterobacteriaceae, *Pseudomonas*, *Moraxella*, *Helicobacter*, *Stenotrophomonas*, *Legionella*, and the like. Typically, by replacing the *Bordetella* ampG gene with a heterologous ampG gene, the amount of tracheal cytoxin (TCT) produced in the resulting strain expresses less than 1% residual TCT activity. In another aspect, the amount of TCT toxin expressed by the resulting strain is between about 0.6% to 1% residual TCT activity or about 0.4% to 3% residual TCT activity or about 0.3% to 5% residual TCT activity.

PTX is a major virulence factor responsible for the systemic effects of *B. pertussis* infections, as well as one of the major protective antigens. Due to its properties, the natural ptx gene can be replaced by a mutated version so that the enzymatically active moiety S1 codes for an enzymatically inactive toxin, but the immunogenic properties of the pertussis toxin are not affected. This can be accomplished by replacing the arginine (Arg) at position 9 of the sequence with a lysine (Lys) (R9K). Furthermore, a glutamic acid (Glu) at position 129 can be replaced with a glycine (Gly) (E129G). Generally these amino acid positions are involved in substrate binding and catalysis, respectively. In other aspects, other mutations can also be made such as those described in U.S.

Pat. No. 6,713,072, incorporated herein by reference, as well as any known or other mutations able to reduce the toxin activity. In one aspect, allelic exchange can first be used to delete the ptx operon and then to insert a mutated version.

In another aspect, the dnt gene can be removed from the Bordetella strain using allelic exchange. Besides the total removal, the enzymatic activity can also be inhibited by a point mutation. Since DNT is constituted by a receptor-binding domain in the N-terminal region and a catalytic domain in the C-terminal part, a point mutation in the dnt gene to replace Cys-1305 to Ala-1305 inhibits the enzyme activity of DNT (Kashimoto T., Katahira J, Cornejo W R, Masuda M, Fukuoh A, Matsuzawa T, Ohnishi T, Horiguchi Y. (1999) Identification of functional domains of Bordetella dermonecrotizing toxin. Infect. Immun. 67: 3727-32.).

Besides allelic exchange to insert the mutated ptx gene and the inhibited or deleted dnt gene, the open reading frame of a gene can be interrupted by insertion of a genetic sequence or plasmid. This method is also contemplated. Other methods of generating mutant strains are generally well known in the art.

In one aspect, the mutated strain is called a BPZE1 strain and has been deposited with the Collection Nationale de Cultures de Microorganismes (CNCM) in Paris, France under the Budapest Treaty on Mar. 9, 2006 and assigned the number CNCM I-3585. The mutations introduced into BPZE1 generally result in attenuation, but also allow the bacteria to colonize and persist. Thus, in another aspect, BPZE1 can induce mucosal immunity and systemic immunity when administered to a mammal in need thereof. In another aspect, a BPZE1 recombinant strain was constructed which expresses three copies of M2e peptide. This strain has been deposited with the National Measurement Institute (formerly AGAL) in Port Melbourne, Victoria, Australia 3207 under the Budapest Treaty on Apr. 27, 2009, and assigned the following accession number V09/009169. M2e is the extracellular portion of the M2 protein from influenza virus. It is highly conserved among all influenza A viruses and has been shown to induce an antibody-mediated protection against influenza A viruses. The recombinant M2e-producing BPZE1 strain can trigger (for example, upon nasal administration of the live bacteria) substantial anti-M2e antibody responses (local and systemic), allowing a significant protection against H1N1 and H3N2 challenge comparable to the BPZE1 bacteria alone.

The mutated Bordetella strains can be used in immunogenic compositions for the treatment or prevention of allergic diseases. Such immunogenic compositions are useful to raise an immune response, either an antibody response and or a T cell response in mammals. For example, the T cell response can be such that it protects a mammal against allergic disease or against its consequences/symptoms.

The mutated Bordetella strains can be used as live strains in vaccines or immunogenic compositions. In one aspect, the live strains are used for nasal administration, while the chemically- or heat killed strains can be used for systemic or mucosal administration. In other aspects the stains are attenuated.

In other aspects, the strains do not include any heterologous genes other than the heterologous ampG gene described above. In yet other aspects, the strains do not include a heterologous expression platform (See, e.g., WO2007104451, herein incorporated by reference). Typically, heterologous expression platforms carry heterologous antigens. In one aspect, the heterologous expression platform can be used to deliver the heterologous antigens to the respiratory mucosa of a mammal.

Formulations and Carriers

Methods for treatment or prevention of allergic diseases are also contemplated. Said methods can include administering a therapeutically effective amount of a composition disclosed herein. The composition can be formulated in pharmaceutical compositions. These compositions can comprise, in addition to one or more of the strains, a pharmaceutically acceptable excipient, carrier, buffer, stabilizer, or other materials well known to those skilled in the art. Such materials should typically be non-toxic and should not typically interfere with the efficacy of the active ingredient. The precise nature of the carrier or other material can depend on the route of administration, e.g., oral, intravenous, cutaneous or subcutaneous, nasal, intramuscular, or intraperitoneal routes.

Compositions can include a pharmaceutically suitable excipient, vehicle, and/or carrier. Compositions can be formulated in a liquid suspension, an aerosol, or a powder.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil, or synthetic oil. Physiological saline solution, dextrose, or other saccharide solution or glycols such as ethylene glycol, propylene glycol, or polyethylene glycol can be included.

For intravenous, cutaneous, or subcutaneous injection, or injection at the site of affliction, the active ingredient will be in the form of a parenterally acceptable aqueous solution which is pyrogen-free and has suitable pH, isotonicity, and stability. Those of relevant skill in the art are well able to prepare suitable solutions using, for example, isotonic vehicles such as Sodium Chloride Injection, Ringer's Injection, or Lactated Ringer's Injection. Preservatives, stabilisers, buffers, antioxidants, and/or other additives can be included, as required.

Administration can be in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of disease being treated. Prescription of treatment, e.g., decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in the latest edition of Remington's Pharmaceutical Science, Mack Publishing Company, Easton, Pa. ("Remington's").

Typically, a composition can be administered alone or in combination with other treatments, either simultaneously or sequentially dependent upon the condition to be treated.

Adjuvants

Compositions can be administered in conjunction with other immunoregulatory agents, including adjuvants. As used herein, the term "adjuvant" refers to a compound or mixture that enhances an immune response. In particular, compositions can include an adjuvant. Adjuvants can include, but are not limited to, one or more of the following set forth below.

Mineral Containing Adjuvant Compositions

Mineral containing compositions suitable for use as adjuvants include mineral salts, such as aluminum salts and calcium salts. The adjuvants includes mineral salts such as hydroxides (e.g., oxyhydroxides), phosphates (e.g., hydroxyphosphates, orthophosphates), sulfates, and the like (e.g., see chapters 8 & 9 of Vaccine Design . . . (1995) eds. Powell & Newman. ISBN: 030644867X. Plenum.), or mixtures of different mineral compounds (e.g., a mixture of a phosphate and a hydroxide adjuvant, optionally with an excess of the phosphate), with the compounds taking any suitable form (e.g., gel, crystalline, amorphous, and the like), and with adsorption to the salt(s) being contemplated. The mineral containing compositions can also be formulated as a particle of metal salt (WO/0023105).

Aluminum salts can be included in compositions such that the dose of $Al_3^+$ is between 0.2 and 1.0 mg per dose.

Oil-Emulsion Adjuvants

Oil-emulsion compositions suitable for use as adjuvants can include squalene-water emulsions, such as MF59 (5% Squalene, 0.5% TWEEN® 80 (POE (20) sorbitan monooleate, Polyethylene glycol sorbitan monooleate, Polyoxyethylenesorbitan monooleate, Polysorbate 80), and 0.5% Span 85, formulated into submicron particles using a microfluidizer). See, e.g., WO90/14837. See also, Podda, "The adjuvanted influenza vaccines with novel adjuvants: experience with the MF59-adjuvanted vaccine", Vaccine 19: 2673-2680, 2001.

In other related aspects, adjuvants for use in the compositions are submicron oil-in-water emulsions. Examples of submicron oil-in-water emulsions for use herein include squalene/water emulsions optionally containing varying amounts of MTP-PE, such as a submicron oil-in-water emulsion containing 4-5% w/v squalene, 0.25-1.0% w/v TWEEN® 80 (POE (20) sorbitan monooleate, Polyethylene glycol sorbitan monooleate, Polyoxyethylenesorbitan monooleate, Polysorbate 80), and/or 0.25-1.0% Span 85 (sorbitan trioleate), and, optionally, N-acetylmuramyl-L-alanyl-0-isogluatminyl-L-alanine-2-(1'-2'-dipalmitoyl-s-n-glycero-3-huydroxyphosphophoryloxy)-ethylamine (MTP-PE), for example, the submicron oil-in-water emulsion known as "MF59" (International Publication No. WO90/14837; U.S. Pat. Nos. 6,299,884 and 6,451,325, incorporated herein by reference in their entirety; and Ott et al., "MF59—Design and Evaluation of a Safe and Potent Adjuvant for Human Vaccines" in Vaccine Design: The Subunit and Adjuvant Approach (Powell, M. F. and Newman, M. J. eds.) Plenum Press, New York, 1995, pp. 277-296). MF59 can contain 4-5% w/v Squalene (e.g., 4.3%), 0.25-0.5% w/v TWEEN® 80 (POE (20) sorbitan monooleate, Polyethylene glycol sorbitan monooleate, Polyoxyethylenesorbitan monooleate, Polysorbate 80), and 0.5% w/v Span 85 and optionally contains various amounts of MTP-PE, formulated into submicron particles using a microfluidizer such as Model 110Y microfluidizer (Microfluidics, Newton, Mass.). For example, MTP-PE can be present in an amount of about 0-500 g/dose, or 0-250 g/dose, or 0-100 g/dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325, incorporated herein by reference in their entirety.

Complete Freund's adjuvant (CFA) and incomplete Freund's adjuvant (IFA) can also be used as adjuvants.

Saponin Adjuvant Formulations

Saponin formulations, can also be used as adjuvants. Saponins are a heterologous group of sterol glycosides and triterpenoid glycosides that are found in the bark, leaves, stems, roots and even flowers of a wide range of plant species. Saponin from the bark of the *Quillaia saponaria Molina* tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations can include purified formulations, such as QS21, as well as lipid formulations, such as Immunostimulating Complexs (ISCOMs; see below).

Saponin compositions have been purified using High Performance Thin Layer Chromatography (HPLC) and Reversed Phase High Performance Liquid Chromatography (RP-HPLC). Specific purified fractions using these techniques have been identified, including QS7, QS17, QS18, QS21, QH-A, QH-B and QH-C. A method of production of QS21 is disclosed in U.S. Pat. No. 5,057,540. Saponin formulations can also comprise a sterol, such as cholesterol (see WO96/33739).

Combinations of saponins and cholesterols can be used to form unique particles called ISCOMs. ISCOMs typically also include a phospholipid such as phosphatidylethanolamine or phosphatidylcholine. Any known saponin can be used in ISCOMs. For example, an ISCOM can include one or more of Quil A, QHA and QHC. ISCOMs are further described in EP0109942, WO96/11711, and WO96/33739. Optionally, the ISCOMS can be devoid of additional detergent. See WO00/07621.

A description of the development of saponin based adjuvants can be found at Barr, et al., "ISCOMs and other saponin based adjuvants", Advanced Drug Delivery Reviews 32: 247-27, 1998. See also Sjolander, et al., "Uptake and adjuvant activity of orally delivered saponin and ISCOM vaccines", Advanced Drug Delivery Reviews 32: 321-338, 1998.

Virosomes and Virus Like Particles (VLPs)

Virosomes and Virus-Like Particles (VLPs) can also be used as adjuvants. These structures generally contain one or more proteins from a virus optionally combined or formulated with a phospholipid. They are generally non-pathogenic, non-replicating and generally do not contain any of the native viral genome. The viral proteins can be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein pl).

Bacterial or Microbial Derivatives

Adjuvants can include bacterial or microbial derivatives such as:

(1) Non-Toxic Derivatives of Enterobacterial Lipopolysaccharide (LPS)

Such derivatives include Monophosphoryl lipid A (MPL) and 3-O-deacylated MPL (3 dMPL). 3 dMPL is a mixture of 3 De-O-acylated monophosphoryl lipid A with 4, 5 or 6 acylated chains. An example of a "small particle" form of 3 De-O-acylated monophosphoryl lipid A is disclosed in EP 0 689 454. Such "small particles" of 3 dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529. See Johnson et al., Bioorg Med Chem Lett 9: 2273-2278, 1999.

(2) Lipid A Derivatives

Lipid A derivatives can include derivatives of lipid A from *Escherichia coli* such as OM-174. OM-174 is described for example in Meraldi et al., "OM-174, a New Adjuvant with a Potential for Human Use, Induces a Protective Response with Administered with the Synthetic C-Terminal Fragment 242-

310 from the circumsporozoite protein of *Plasmodium berghei*", *Vaccine* 21: 2485-2491, 2003; and Pajak, et al., "The Adjuvant OM-174 induces both the migration and maturation of murine dendritic cells in vivo", *Vaccine* 21: 836-842, 2003.

(3) Immunostimulatory Oligonucleotides

Immunostimulatory oligonucleotides suitable for use as adjuvants can include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's can include nucleotide modifications/analogs such as phosphorothioate modifications and can be double-stranded or single-stranded. Optionally, the guanosine can be replaced with an analog such as 2'-deoxy-7-deazaguanosine. See Kandimalla, et al., "Divergent synthetic nucleotide motif recognition pattern: design and development of potent immunomodulatory oligodeoxyribonucleotide agents with distinct cytokine induction profiles", *Nucleic Acids Research* 31: 2393-2400, 2003; WO02/26757 and WO99/62923 for examples of analog substitutions. The adjuvant effect of CpG oligonucleotides is further discussed in Krieg, "CpG motifs: the active ingredient in bacterial extracts?", Nature Medicine (2003) 9(7): 831-835; McCluskie, et al., "Parenteral and mucosal prime-boost immunization strategies in mice with hepatitis B surface antigen and CpG DNA", FEMS Immunology and Medical Microbiology (2002) 32:179-185; WO98/40100; U.S. Pat. No. 6,207,646; U.S. Pat. No. 6,239, 116 and U.S. Pat. No. 6,429,199.

The CpG sequence can be directed to Toll-like receptor (TLR9), such as the motif GTCGTT or TTCGTT. See Kandimalla, et al., "Toll-like receptor 9: modulation of recognition and cytokine induction by novel synthetic CpG DNAs", Biochemical Society Transactions (2003) 31 (part 3): 654-658. The CpG sequence can be specific for inducing a Th1 immune response, such as a CpG-A ODN, or it can be more specific for inducing a B cell response, such a CpG-B ODN. CpG-A and CpG-B ODNs are discussed in Blackwell, et al., "CpG-A-Induced Monocyte IFN-gamma-Inducible Protein-10 Production is Regulated by Plasmacytoid Dendritic Cell Derived IFN-alpha", *J. Immunol.* 170: 4061-4068, 2003; Krieg, "From A to Z on CpG", *TRENDS in Immunology* 23: 64-65, 2002, and WO01/95935.

In some aspects, the CpG oligonucleotide can be constructed so that the 5' end is accessible for receptor recognition. Optionally, two CpG oligonucleotide sequences can be attached at their 3' ends to form "immunomers". See, for example, Kandimalla, et al., "Secondary structures in CpG oligonucleotides affect immunostimulatory activity", *BBRC* 306: 948-95, 2003; Kandimalla et al., "Toll-like receptor 9: modulation of recognition and cytokine induction by novel synthetic GpG DNAs", *Biochemical Society Transactions* 31: 664-658, 2003; Bhagat et al., "CpG penta- and hexadeoxyribonucleotides as potent immunomodulatory agents" *BBRC* 300: 853-861, 2003, and WO03/035836.

(4) ADP-Ribosylating Toxins and Detoxified Derivatives Thereof.

Bacterial ADP-ribosylating toxins and detoxified derivatives thereof can be used as adjuvants. For example, the toxin can be derived from *E. coli* (i.e., *E. coli* heat labile enterotoxin (LT)), cholera (CT), or pertussis (PTX). The use of detoxified ADP-ribosylating toxins as mucosal adjuvants is described in WO95/17211 and as parenteral adjuvants in WO98/42375. In some aspects, the adjuvant can be a detoxified LT mutant such as LT-K63, LT-R72, and LTR192G. The use of ADP-ribosy- lating toxins and detoxified derivatives thereof, particularly LT-K63 and LT-R72, as adjuvants can be found in the following references, each of which is specifically incorporated by reference herein in their entirety: Beignon, et al., "The LTR72 Mutant of Heat-Labile Enterotoxin of *Escherichia coli* Enhances the Ability of Peptide Antigens to Elicit CD4+T Cells and Secrete Gamma Interferon after Coapplication onto Bare Skin", *Infection and Immunity* 70: 3012-3019, 2002; Pizza, et al., "Mucosal vaccines: non toxic derivatives of LT and CT as mucosal adjuvants", Vaccine 19: 2534-2541, 2001; Pizza, et al., "LTK63 and LTR72, two mucosal adjuvants ready for clinical trials" *Int. J. Med. Microbiol.* 290: 455-461, 2003; Scharton-Kersten et al., "Transcutaneous Immunization with Bacterial ADP-Ribosylating Exotoxins, Subunits and Unrelated Adjuvants", *Infection and Immunity* 68: 5306-5313, 2000; Ryan et al., "Mutants of *Escherichia coli* Heat-Labile Toxin Act as Effective Mucosal Adjuvants for Nasal Delivery of an Acellular Pertussis Vaccine: Differential Effects of the Nontoxic AB Complex and Enzyme Activity on Th1 and Th2 Cells" *Infection and Immunity* 67: 6270-6280, 2003; Partidos et al., "Heat-labile enterotoxin of *Escherichia coli* and its site-directed mutant LTK63 enhance the proliferative and cytotoxic T-cell responses to intranasally co-immunized synthetic peptides", *Immunol. Lett.* 67: 09-216, 1999; Peppoloni et al., "Mutants of the *Escherichia coli* heat-labile enterotoxin as safe and strong adjuvants for intranasal delivery of vaccines", *Vaccines* 2: 285-293, 2003; and Pine et al., (2002) "Intranasal immunization with influenza vaccine and a detoxified mutant of heat labile enterotoxin from *Escherichia coli* (LTK63)" *J. Control Release* 85: 263-270, 2002. Numerical reference for amino acid substitutions can be based on the alignments of the A and B subunits of ADP-ribosylating toxins set forth in Domenighini et al., *Mol. Microbiol.* 15: 1165-1167, 1995, specifically incorporated herein by reference in its entirety.

Bioadhesives and Mucoadhesives

Bioadhesives and mucoadhesives can also be used as adjuvants. Suitable bioadhesives can include esterified hyaluronic acid microspheres (Singh et al., *J. Cont. Rele.* 70:267-276, 2001) or mucoadhesives such as cross-linked derivatives of poly(acrylic acid), polyvinyl alcohol, polyvinyl pyrollidone, polysaccharides and carboxymethylcellulose. Chitosan and derivatives thereof can also be used as adjuvants. See, for example, WO99/27960.

Adjuvant Microparticles

Microparticles can also be used as adjuvants. Microparticles (i.e., a particle of about 100 nm to about 150 μm in diameter, or 200 nm to about 30 μm in diameter, or about 500 nm to about 10 μm in diameter) formed from materials that are biodegradable and/or non-toxic (e.g., a poly(alpha-hydroxy acid), a polyhydroxybutyric acid, a polyorthoester, a polyanhydride, a polycaprolactone, and the like), with poly (lactide-co-glycolide) are envisioned, optionally treated to have a negatively-charged surface (e.g., with SDS) or a positively-charged surface (e.g., with a cationic detergent, such as CTAB).

Adjuvant Liposomes

Examples of liposome formulations suitable for use as adjuvants are described in U.S. Pat. No. 6,090,406, U.S. Pat. No. 5,916,588, and EP 0 626 169.

I. Polyoxyethylene Ether and Polyoxyethylene Ester Formulations

Adjuvants can also include polyoxyethylene ethers and polyoxyethylene esters. WO99/52549. Such formulations can further include polyoxyethylene sorbitan ester surfactants in combination with an octoxynol (WO01/21207) as well as polyoxyethylene alkyl ethers or ester surfactants in combination with at least one additional non-ionic surfactant such as an octoxynol (WO01/21152).

In some aspects, polyoxyethylene ethers can include: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, or polyoxyethylene-23-lauryl ether.

Polyphosphazene (PCPP)

PCPP formulations for use as adjuvants are described, for example, in Andrianov et al., "Preparation of hydrogel microspheres by coacervation of aqueous polyphosphazene solutions", *Biomaterials* 19: 109-115, 1998, and Payne et al., "Protein Release from Polyphosphazene Matrices", *Adv. Drug. Delivery Review* 31: 185-196, 1998.

Muramyl Peptides

Examples of muramyl peptides suitable for use as adjuvants can include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphosphoryloxy)-ethylamine MTP-PE).

Imidazoquinolone Compounds.

Examples of imidazoquinolone compounds suitable for use as adjuvants can include Imiquimod and its homologues, described further in Stanley, "Imiquimod and the imidazoquinolones: mechanism of action and therapeutic potential" *Clin Exp Dermatol* 27: 571-577, 2002 and Jones, "Resiquimod 3M", *Curr Opin Investig Drugs* 4: 214-218, 2003.

Human Immunomodulators

Human immunomodulators suitable for use as adjuvants can include cytokines, such as interleukins (e.g., IL-1, IL-2, IL-4, IL-5, IL-6, IL-7, IL-12, and the like), interferons (e.g., interferon-gamma), macrophage colony stimulating factor, and tumor necrosis factor.

Adjuvant Combinations

Adjuvants can also comprise combinations of aspects of one or more of the adjuvants identified above. For example, adjuvant compositions can include:

(1) a saponin and an oil-in-water emulsion (WO99/11241);

(2) a saponin (e.g., QS21)+a non-toxic LPS derivative (e.g., 3 dMPL) (see WO94/00153);

(3) a saponin (e.g., QS21)+a non-toxic LPS derivative (e.g., 3 dMPL)+a cholesterol;

(4) a saponin (e.g., QS21)+3 dMPL+IL-12 (optionally+a sterol) (WO98/57659);

(5) combinations of 3dMPL with, for example, QS21 and/or oil-in-water emulsions (See European patent applications 0835318, 0735898 and 0761231);

(6) SAF, containing 10% Squalane, 0.4% TWEEN® 80 (POE (20) sorbitan monooleate, Polyethylene glycol sorbitan monoleate, Polyoxyethylenesorbitan monooleate, Polysorbate 80), 5% pluronic-block polymer L121, and thr-MDP, either microfluidized into a submicron emulsion or vortexed to generate a larger particle size emulsion.

(7) Ribi adjuvant system (RAS), (Ribi Immunochem) containing 2% Squalene, 0.2% TWEEN® 80 (POE (20) sorbitan monooleate, Polyethylene glycol sorbitan monooleate, Polyoxyethylenesorbitan monooleate, Polysorbate 80), and one or more bacterial cell wall components from the group consisting of monophosphory lipid A (MPL), trehalose dimycolate (TDM), and cell wall skeleton (CWS), e.g., MPL+CWS (Detox); and (8) one or more mineral salts (such as an aluminum salt)+a non-toxic derivative of LPS (such as 3 dPML).

Aluminum salts and MF59 are examples of adjuvants for use with injectable vaccines. Bacterial toxins and bioadhesives are examples of adjuvants for use with mucosally-delivered vaccines, such as nasal vaccines. All adjuvants noted above and others as generally known in the art to one of ordinary skill can be formulated for intranasal administration using techniques well known in the art.

Methods

Administration Routes

Compositions will generally be administered directly to a mammal. Direct delivery can be accomplished by parenteral injection (e.g., subcutaneously, intraperitoneally, intradermal, intravenously, intramuscularly, or to the interstitial space of a tissue), or mucosally, such as by rectal, oral (e.g., tablet, spray), vaginal, topical, transdermal (See e.g., WO99/27961) or transcutaneous (See e.g., WO02/074244 and WO02/064162), inhalation, intranasal (See e.g., WO03/028760), ocular, aural, pulmonary or other mucosal administration. Compositions can also be administered topically by direct transfer to the surface of the skin. Topical administration can be accomplished without utilizing any devices, or by contacting naked skin with the composition utilizing a bandage or a bandage-like device (see, e.g., U.S. Pat. No. 6,348,450). In some aspects, a composition can be administered via the nose of the subject, e.g., intranasally or via inhalation.

In some aspects, the mode of administration is parenteral, mucosal, or a combination of mucosal and parenteral immunizations. In other aspects, the mode of administration is parenteral, mucosal, or a combination of mucosal and parenteral immunizations in a total of 1-2 vaccinations 1-3 weeks apart. In related aspects, the route of administration includes but is not limited to intranasal delivery.

Administration Procedures and Dosages

Administration can include administration of a mutated *Bordetella* strain to a mammal to elicit an immune response (e.g., a TH1 immune response) capable of impacting an allergic disease, e.g., asthma or skin inflammation. Examples of mutated *Bordetella* strains described above. Typically, administration of the mutated *Bordetella* strain is used to treat or prevent an allergic disease in a mammal, e.g., a human, via protective immunity against the allergy. In some aspects, the mutated *Bordetella* strain administration is used to prevent allergic disease by administration prior to the diagnosis of allergic disease or development of allergic disease symptoms or development of allergic disease. Typically, the mutated *Bordetella* stain is administered to a mammal about less than 1, 1, 2, 3, 4, 5, 6, 7, 8, 9, 10, 11, 12, or more weeks prior to the development of allergic disease.

In one aspect, the method for treating or preventing allergic disease includes administering to a subject in need thereof a single dose of a composition, e.g., BPZE1. In related aspects, the administering step is performed mucosally, e.g., intranasally.

In some aspects, a composition is administered in one dose to a subject. In other aspects, a composition is administered in more than one dose, e.g., two doses. In some aspects, a composition is administered in 1, 2, 3, 4, or greater than 4 doses. The number of doses can vary as needed, for example the number of doses administered to a mammal can be 1, 2, 3, 4, 5, 6, 7, 8, 9, 10, or more doses. In one aspect, the method for treating or preventing an allergic disease, includes administering to a subject in need thereof a first immunogenic composition (comprising e.g., BPZE1) followed by a second immunogenic composition administration (comprising e.g., BPZE1). Typically, the time range between each dose of the composition can be about 1-6 days, or about 1, 2, 3, 4, 5, 6, 7, 8, 9, 10, 11, 12, 13, 14, 15, 20, 30, 40, 50, 60, 70, 80, 90, or more weeks. In related aspects, the time range between each dose is about 3 weeks. In other aspects, prime-boost-style methods can be employed where a composition can be delivered in a "priming" step and, subsequently, a composition is delivered in a "boosting" step.

The composition can typically be used to elicit systemic and/or mucosal immunity, for example to elicit an enhanced systemic and/or mucosal immunity. For example, the immune response can be characterized by the induction of a serum IgG and/or intestinal IgA immune response. Typically, the level of protection against allergic disease can be more than 50%, e.g., 60%, 70%, 80%, 90%, 91%, 92%, 93%, 94%, 95%, 96%, 97%, 98%, 99%, or more. In one aspect, the level of protection can be 100%. In other aspects the level of protection is less than 50%, e.g., 20%. In other aspects, the number of bacteria in each dosage is adjusted to attain an effective immune response in a mammal. The number of bacteria or cfus in each dosage can be about 1, 10, 100, 1000, 10000, 100000, 1000000, $5 \times 10^6$, or more or any dosage between said each dosage. In some aspects, the number of CFUs in a dosage or set of dosages can be less than $10^6$, $10^6$, $10^7$, $10^8$, $10^9$, $10^{10}$, greater than $10^{10}$, or from about $10^6$ to about $10^{10}$ colony forming units (CFUs).

In other aspects administration of a composition can also include co-administration of the composition with another agent or agents. Typically the various compositions/agents can be delivered in any order. Thus, in aspects including delivery of multiple different compositions or agents, the mutated *Bordetella* strain need not be all delivered before the agent, e.g., a drug, a siRNA, a miRNA, an immunogenic peptide, or a small molecule capable of affecting an allergic disease. Other examples of agents include neuraminidase inhibitors and M2 inhibitors (adamantanes). For example, the priming step can include delivery of one or more agents and the boosting can include delivery of one or more mutated *Bordetella* strains. In other aspects, multiple administrations of mutated *Bordetella* strains can be followed by multiple administrations of agents. Administrations can be performed in any order. Thus, one or more of the mutated *Bordetella* strains described herein and one or more agents can be co-administered in any order and via any administration route known in the art, e.g., to elicit an immune reaction.

Dosage treatment can be according to a single dose schedule or a multiple dose schedule. For example, multiple doses can be used in a primary immunization schedule and/or in a booster immunization schedule. In a multiple dose schedule, the various doses can be given by the same or different routes, e.g., a parenteral prime and mucosal boost, a mucosal prime and parenteral boost, and the like In other aspects, the dosage regime can enhance the avidity of the antibody response leading to antibodies with a neutralizing characteristic. An in-vitro neutralization assay can be used to test for neutralizing antibodies (see for example Asanaka et al, *J Virology* 102: 10327, 2005; Wobus et al., *PLOS Biology* 2; e432; and Dubekti et al., *J Medical Virology* 66: 400).

Tests to Determine the Efficacy or Presence of an Immune Response

One way of assessing efficacy of therapeutic treatment involves monitoring infection after administration of a composition. One way of assessing efficacy of prophylactic treatment involves monitoring immune responses against the antigens in the compositions after administration of the composition. Another way of assessing the immunogenicity of the compositions is to isolate the proteins or proteins mixes and to screen patient sera or mucosal secretions by immunoblot. A positive reaction between the protein and the patient serum indicates that the patient has previously mounted an immune response to the composition.

Another way of checking efficacy of therapeutic treatment involves monitoring infection after administration of the compositions. One way of checking efficacy of prophylactic treatment involves monitoring immune responses both systemically (such as monitoring the level of IgG1 and IgG2a production) and mucosally (such as monitoring the level of IgA production) against the antigens in the compositions after administration of the composition. Typically, serum specific antibody responses are determined post-immunization but pre-challenge whereas mucosal specific antibody responses are determined post-immunization and post-challenge. The immunogenic compositions can be evaluated in in vitro and in vivo animal models prior to host, e.g., human, administration.

The efficacy of compositions can also be determined in vivo by challenging animal models of infection, e.g., mice, with the compositions. The compositions can or can not be derived from the same strains as the challenge strains. In vivo efficacy models can include but are not limited to: (i) A murine infection model using human strains; (ii) a murine disease model which is a murine model using a mouse-adapted strain, such as strains which are particularly virulent in mice; and (iii) a primate model using human isolates.

The immune response can be one or both of a TH1 immune response and a TH2 response. The immune response can be an improved or an enhanced or an altered immune response. The immune response can be one or both of a systemic and a mucosal immune response. For example, the immune response can be an enhanced systemic and/or mucosal response. An enhanced systemic and/or mucosal immunity is reflected in an enhanced TH1 and/or TH2 immune response. For example, the enhanced immune response can include an increase in the production of IgG1 and/or IgG2a and/or IgA. In another aspect the mucosal immune response can be a TH2 immune response. For example, the mucosal immune response can include an increase in the production of IgA.

Typically, activated TH2 cells enhance antibody production and are therefore of value in responding to extracellular infections. Activated TH2 cells can typically secrete one or more of IL-4, IL-5, IL-6, and IL-10. A TH2 immune response can also result in the production of IgG1, IgE, IgA, and/or memory B cells for future protection. In general, a TH2 immune response can include one or more of an increase in one or more of the cytokines associated with a TH2 immune response (such as IL-4, IL-5, IL-6 and IL-10), or an increase in the production of IgG1, IgE, IgA and memory B cells. For example, an enhanced TH2 immune response can include an increase in IgG1 production.

A TH1 immune response can include one or more of an increase in CTLs, an increase in one or more of the cytokines associated with a TH1 immune response (such as IL-2, IFN-gamma, and TNF-alpha), an increase in activated macrophages, an increase in NK activity, or an increase in the production of IgG2a. For example, the enhanced TH1 immune response can include an increase in IgG2a production.

Compositions, in particular, an immunogenic composition comprising one or more strains disclosed herein can be used either alone or in combination with other agents optionally with an immunoregulatory agent capable of eliciting a Th1 and/or Th2 response.

The compositions can elicit both a cell-mediated immune response as well as a humoral immune response to effectively address an allergic disease. This immune response can induce long lasting (e.g., neutralizing) antibodies and a cell-mediated immunity that can quickly respond in the future.

Subjects and Mammals

Compositions are typically for preventing or treating allergic disease in a subject, e.g., a mammal or a human. In some aspects, subjects can include the elderly (e.g., >65 years old), children (e.g., <5 years old), hospitalized patients, healthcare workers, armed service and military personnel, food handlers, pregnant women, the chronically ill, and people traveling abroad. The compositions are generally suitable for these groups as well as the general population or as otherwise deemed necessary by a physician.

In some aspects, a subject is identified as being need of composition administration. In some aspects, a subject is identified as being need of composition administration via an assay. In some aspects, the assay can be a pharmacogenetic test, an asthma predictive index based on wheezing, and an asthma control test (ACT). In some aspects, a test or assay that is useful for identifying a subject in need of composition administration is described in: Wu et al., Development of a Pharmacogenetic Predictive Test in asthma: proof of concept, Pharmacogenet Genomics. 2010 February; 20(2):86-93; Castro-Rodriguez J A; The Asthma Predictive Index: a very useful tool for predicting asthma in young children; J Allergy Clin Immunol. 2010 August; 126(2):212-6; the Asthma Control Test (ACT) available at the website of QualityMetric on Oct. 24, 2012; Marzulli F N et al., Contact allergy: predictive testing in man, Contact Dermatitis. 1976 February; 2(1):1-17; and Tupker et al., Prediction of Skin Irritation by Noninvasive Bioengineering Methods, Abstract (each of which is herein incorporated by reference in its entirety).

Kits

Also provided are kits that include one or more containers of compositions. Compositions can be in liquid form or can be lyophilized. Suitable containers for the compositions include, for example, bottles, vials, syringes, and test tubes. Containers can be formed from a variety of materials, including glass or plastic. A container can have a sterile access port (for example, the container can be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device(s). The kit can further include a third component comprising an adjuvant.

The kit can also comprise a package insert containing written instructions for methods of inducing immunity, preventing infections, or for treating infections. Instructions can be instructions for performing one or more methods described herein. The package insert can be an unapproved draft package insert or can be a package insert approved by the Food and Drug Administration (FDA) or other regulatory body.

Also provided is a delivery device pre-filled with the compositions.

The pharmaceutical compositions are generally formulated as sterile, substantially isotonic and in full compliance with all Good Manufacturing Practice (GMP) regulations of the U.S. Food and Drug Administration.

From the foregoing description, various modifications and changes in the compositions and methods will occur to those skilled in the art. All such modifications coming within the scope of the appended claims are intended to be included therein. Each recited range includes all combinations and sub-combinations of ranges, as well as specific numerals contained therein.

Although the foregoing aspects of the invention have been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

EXEMPLARY ASPECTS

Below are examples of specific aspects for carrying out various aspects of the invention. The examples are offered for illustrative purposes only, and are not intended to limit the scope of the various aspects of the invention in any way. Efforts have been made to ensure accuracy with respect to numbers used (e.g., amounts, temperatures, and the like), but some experimental error and deviation should, of course, be allowed for.

The practice of the various aspects of the invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's*; Carey and Sundberg *Advanced Organic Chemistry* $3^{rd}$ Ed. (Plenum Press) Volumes A and B, 1992).

Materials and Methods

Bacterial Strains and Growth Conditions

Attenuated *B. pertussis* BPZE1 is a streptomycin-resistant *B. pertussis* Tohama I derivative, lacking dermonecrotic toxin, producing inactivated pertussis toxin and background levels of tracheal cytotoxin (15). Virulent *B. pertussis* BPSM (16) and BPZE1 were cultured as described previously (1).

Animal Experiments

Female BALB/c mice (6-8 weeks old) were purchased from CARE Centre (Singapore). Mice were kept under specific pathogen-free conditions in individual ventilated cages. All animal experiments were approved and carried out according to the Institutional guidelines set by the Animal Care and Use Committee of National University of Singapore.

Briefly, lightly anesthetized mice were intranasally (in.) administered once or twice at a four-week interval with $5\times10^6$ colony forming units (CFU) of live attenuated BPZE1 or BPSM bacteria as previously described (1). Six weeks after one BPZE1 or BPSM dose, or 2 weeks after the $2^{nd}$ dose (day 42), after complete bacterial clearance from the lungs (data not shown), sensitization and challenge were performed as follows: For the allergic airway inflammation model, ovalbumin (OVA) sensitization consisted of two intraperitoneal (ip.) injections of 0.1 ml of 200 μg/ml OVA with Aluminium hydroxide at a 2 week-interval. OVA aerosol challenge was performed 1 week after the last OVA ip. injection for 3 consecutive days as described previously (17). Positive control mice received phosphate-buffered saline (PBS) in. instead of bacteria followed by OVA sensitization and challenge. Negative control mice were OVA-sensitized but challenged with PBS.

In the dinitrochlorobenzene (DNCB)-induced CHS model, mice were sensitized by applying 50 μl of 1% w/v DNCB (Sigma) dissolved in acetone and olive oil (4:1; v/v) on their shaved back. Five days after sensitization (day 47), 25 μl/side of 1% DNCB were applied on both sides of both ears. Negative control mice were sensitized and challenged with acetone and olive oil (4:1; v/v) without DNCB. Ear thickness was monitored daily after challenge using a caliper.

Cellular Infiltrates in Bronchoalveolar Lavage Fluids Mice were euthanized 24 hours after the last aerosol OVA challenge (day 66), and bronchoalveolar lavage fluids (BALFs) were harvested as described previously (17). BALFs were centrifuged, and the supernatants were stored at −80° C. for cytokine detection. The cell pellets were resuspended, spotted onto a glass slide using a CYTOSPIN® device (benchtop centrifuge) (Thermo Shandon), and stained using a modified Wright staining procedure as described previously (17). A total of 500 cells were examined for each slide. Counts were performed on blinded samples. Eight mice per group were individually assessed Antibody and Cytokine Detection The serum levels of total IgE, and OVA-specific IgE, IgG1, and IgG2a were determined by ELISA as described previously (18). Cytokine levels were measured in the BALFs supernatants (allergic airway inflammation model) or ear homogenates (CHS model) using a custom-made multiplex cytokine detection assay (BIO-PLEX®, detection and quantification system, (Biorad) according to the manufacturer's instructions. Ear homogenates were prepared on ice upon addition of 200 µl RIPA buffer (Sigma) with protease inhibitor and mechanical homogenization using High Shear homogenizer (Omni International). After centrifugation at 10,000 rpm and 4° C. to remove the cellular debris, the supernatants were analyzed using a BIO-PLEX® instrument (Bio-Rad).

In Vitro Re-Stimulation Experiment

Since cell suspensions from auricular lymph nodes were prepared and $2 \times 10^6$ Cells/well were seeded in 96-well round-bottom plates (Nunc) in 100 µl RPMI complete medium (RPMI 640 supplemented with 10% FCS, $5 \times 10^{-5}$ M β-mercaptoethanol, 2 mM L-glutamine, 10 mM HEPES, 200 U/ml penicillin, 200 µg/ml of plate-bound anti-CD3 (cat#553057) and 1 µg/ml soluble anti-CD28 (cat#553294) (BD). After 24 h incubation, the supernatants were harvested for Interferon (IFN)-γ measurement using Mouse IFN-γ ELISA Ready-SET-Go!® detection kit (eBioscience, San Diego, Calif.) according to the manufacturer's instructions. The cells were pulsed with 0.4 µCi [3H] thymidine in 20 µl RPMI complete medium. After 18 h incubation, cells were harbested, washed and the incorporated radioactivity was measure in a TOP-COUNT® NXT™ microplate scintillation and luminescence counter (PerkinElmer). Each sample was assayed in triplicate.

Histological Analyses

The lungs or ears were harvested from euthanized mice, fixed in 4% formalin in PBS, embedded in paraffin, sectioned, stained with hematoxylin and eosin (H&E) and examined under an inverted light microscope at ×100 and ×400 magnifications. Alternatively, lung sections were stained with periodic acid-fluorescence Schiff stain (PAFS) and examined for mucus production as described previously (19).

Statistical Analysis

Unless otherwise stated, bars represent mean±SEM, and averages were compared using a bidirectional unpaired Student's t test with a 5% significance level at * $p \leq 0.05$,  $p \leq 0.01$ and * $p \leq 0.001$. For DNCB-induced CHS model, ear thickness data were analyzed by 2-way ANOVA. Values shown are the mean±SEM.

Example 1

Intranasal Pre-Treatment with BPZE1 Provides Long-Term Protection Against OVA-Induced Allergic Asthma Adult BALB/c mice were intranasally (in.) administered either once or twice with live BPZE1 or PBS. After complete bacterial clearance from the lungs (data not shown), OVA-sensitization and challenge were performed. In contrast to the sensitized but not challenged animals (OVA/saline), typical inflammation of the airway walls with marked infiltration of inflammatory cells into the peribronchiolar and perivascular connective tissues was observed with the sensitized and challenged animals (OVA/OVA) (FIG. 1A). Nasal pre-treatment with BPZE1 (one or two doses) visibly reduced peribronchial inflammation (FIG. 1A, c,d,h,i), whereas enhanced pathology was observed in mice pre-treated with virulent *B. pertussis* BPSM (FIG. 1A, e&f). PAFS staining revealed that OVA-induced mucus hypersecretion and goblet cell hyperplasia were noticeably reduced in the BPZE1 pre-treated mice whereas pre-exposure to virulent BPSM did not result in reduction compared to the untreated challenged animals (OVA/OVA) (FIG. 1B). Together, these data indicate that BPZE1 nasal pre-treatment reduces the pathological manifestations of OVA-induced allergic airway inflammation, whereas pre-infection with its virulent counterpart (BPSM) does not.

Example 2

Figure 2:
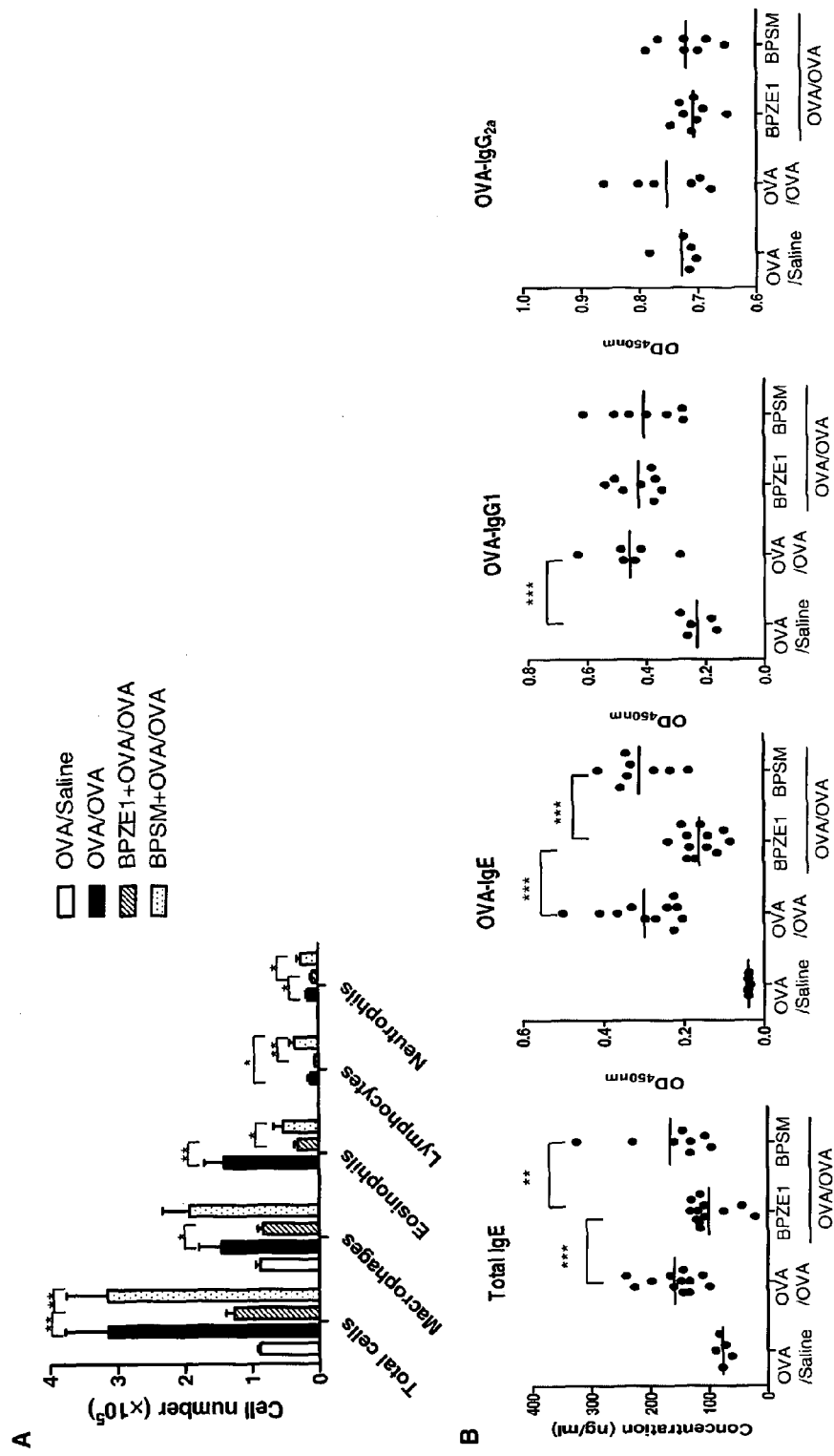
FIG. 2. Effects of BPZE1 pre-treatment on the cellular infiltration in broncho-alveolar lavage fluids and OVA-specific antibody responses upon OVA challenge. A) Inflammatory cell counts in the BALFs were obtained from the different mouse groups 24 hours after the last saline (n=6) or OVA (n=8) aerosol challenge. Differential cell counts were performed blindly on a minimum of 500 cells/slide to identify eosinophils, macrophages, neutrophils, and lymphocytes. * $P \leq 0.05$,  $P \leq 0.01$. (B) Mouse serum from the different groups (n=5-12 mice per group) was collected 24 hours after the last saline or OVA aerosol challenge. The levels of total IgE, OVA-specific IgE, IgG1, and IgG2a were determined by ELISA on individual sera diluted 1/5 (A-B), 1/300,000 (C) or 1/10,000 (D).  $P \leq 0.01$, *** $P \leq 0.001$.

BPZE1 Pre-Treatment Suppresses Ova-Induced Inflammatory Cell Recruitment in the Lungs Examination of the inflammatory cell influx in the BALFs collected 24 hours after OVA challenge showed a marked increase in total cell, eosinophil, macrophage, neutrophil and lymphocyte counts in the sensitized and challenged (OVA/OVA) control animals compared to the non-challenged (OVA/saline) group (FIG. 2A). BPSM pre-treated animals displayed comparable cell counts to those measured in the OVA/OVA control group. In contrast, the total cell, eosinophil, macrophage, neutrophil and lymphocyte counts in the BALFs from BPZE1-treated mice were significantly decreased (FIG. 2A), demonstrating that a single nasal dose of BPZE1 significantly suppressed OVA-induced inflammatory cell recruitment in the lungs.

Example 3

BPZE1 Pre-Treatment Reduces Serum IgE Production

ELISA data indicated a marked elevation in total serum IgE, OVA-specific IgE and OVA-specific IgG1 levels, but not in the OVA-specific IgG2a level in the OVA/OVA mice compared with the OVA/saline group (FIG. 2B). Pre-treatment with BPSM gave antibody levels comparable to those measured in the OVA/OVA group. In contrast, the total serum and OVA-specific IgE levels were strongly reduced in the BPZE1-treated mice whereas BPZE1 pre-treatment had no effect on the serum levels of OVA-specific IgG2a and IgG1 (FIG. 2B). Thus, in. pre-treatment with BPZE1 did not modulate the serum OVA-specific IgG responses, but suppressed the production of total and antigen-specific IgE.

Example 4

Figure 3:
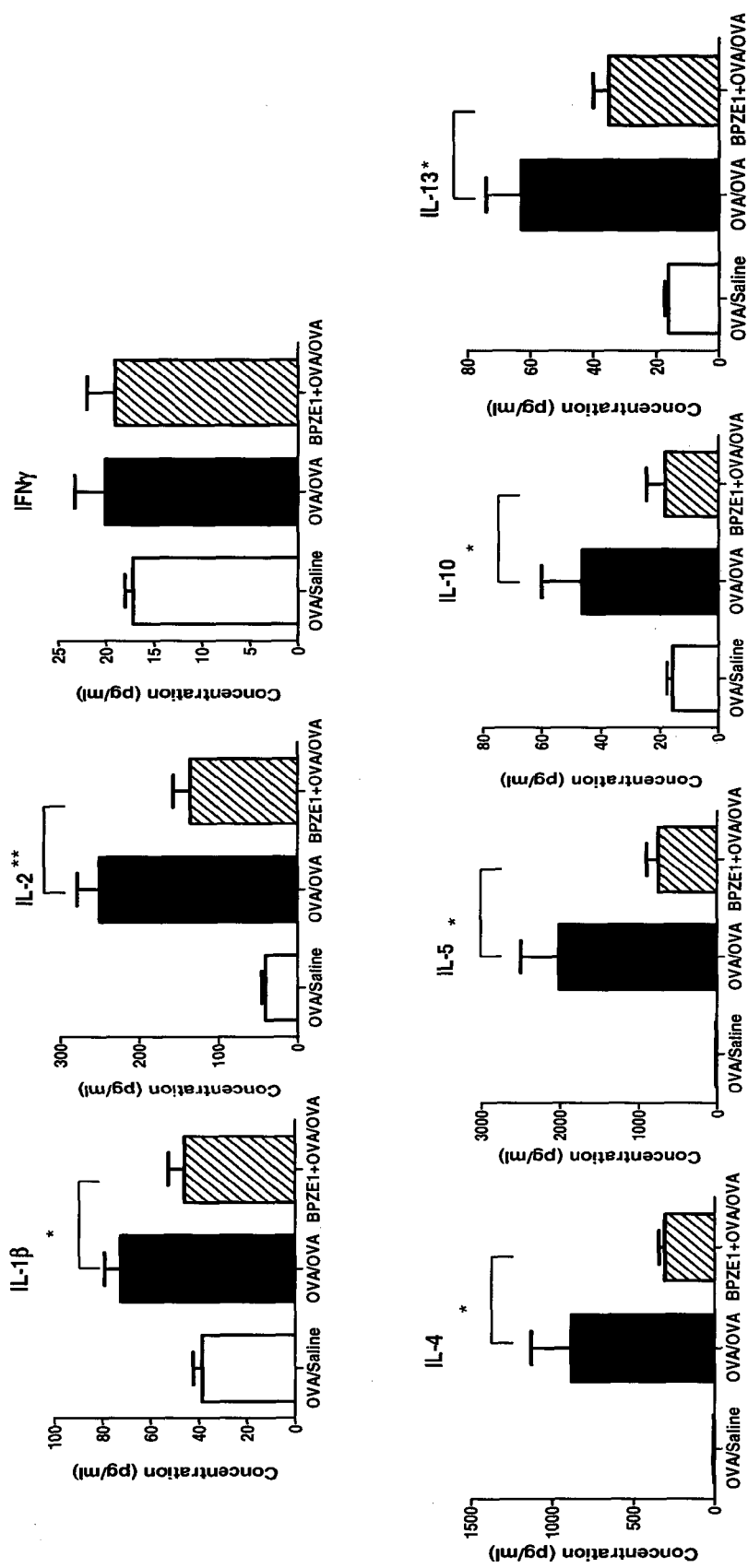
FIG. 3. Effects of BPZE1 pre-treatment on the local cytokine production in the OVA-induced airway inflammation model. BALFs from OVA/Saline, OVA/OVA, BPZE1+OVA/OVA groups (n=6 mice per group) were collected 24 hours after the last saline or OVA aerosol challenge. The levels of cytokines (as indicated) were determined by multiplex assay. Values shown are the mean±SEM. * $P \leq 0.05$, ** $P \leq 0.01$.

BPZE1 Pre-Treatment Reduces OVA-Induced Inflammatory Cytokine Production in BALFs The levels of Th1 (IL-1β, IL-2 and IFN-γ) and Th2 (IL-4, IL-5, IL-13) cytokines, as well as IL-10 were determined in the BALFs. As expected and as reported previously (9,12,20, 21), OVA sensitization and challenge triggered a significant increase in IL-4, IL-5, IL-13, IL-10, IL-1β, and IL-2 levels in the BALFs compared with saline aerosol controls (FIGS. 3A&B, D-G), whereas the level of IFN-γ remained unchanged (FIG. 3C). BPZE1 pre-treatment significantly reduced the production of all the cytokines tested except IFN-γ, suggesting that BPZE1 pre-treatment affects the production of major Th2 and Th1 pro-inflammatory cytokines involved in the pathogenesis of allergic airway inflammation.

Example 5

BPZE1 I.N. Pre-Treatment Inhibits the Progression of DNCB-Induced CHS

Figure 4:
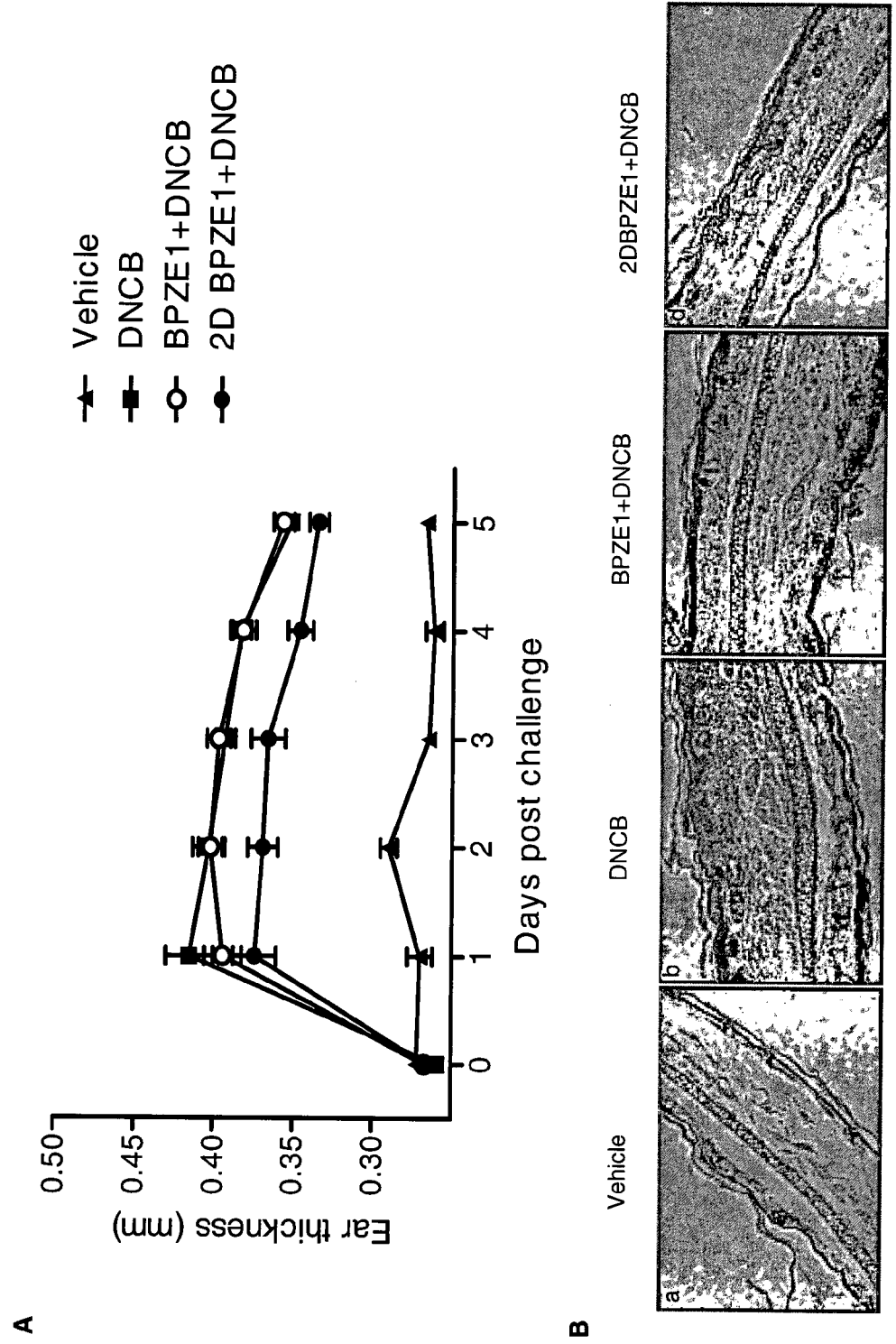
FIG. 4. Effect of BPZE1 pre-treatment on ear thickness (A) and histology (B) in the DNCB-induced CHS mouse model. Mice were treated with BPZE1 once or twice before DNCB sensitization and challenge as indicated in FIG. 1 (C&D). (A) Ear thickness was measured daily using a caliper (n=5 mice per group). Data were analyzed by 2-way ANOVA. Significant differences were observed between BPZE1 (2 doses)-treated group and BPZE1 (1 dose)-treated group/untreated group after DNCB challenge. Values shown are the mean±SEM. (B) H&E staining of ear sections. Observations were made at 100× magnification.

The anti-inflammatory effect of BPZE1 was further investigated in the DNCB-induced ear swelling mouse model of CHS, a Th1 dominated allergic contact dermatitis. Mice were pre-treated i.n. with BPZE1 either once or twice, and after complete bacterial clearance from the lungs, they were sensitized and challenged with DNCB. The protective efficacy of BPZE1 pre-treatment against ear swelling was evaluated by measuring the ear thickness daily after DNCB challenge. Exposure to DNCB resulted in a marked increase in skin thickness 24 hrs after challenge, which was sustained for up to 4 days (FIG. 4). Two doses of BPZE1 significantly inhibited ear swelling in the DNCB-challenged mice (FIG. 4A).

Histological analyses of the ear skin collected 48 hrs after DNCB challenge showed vascular congestion and significant swelling with characteristic tissue edema and pronounced inflammatory infiltrate in the DNCB-challenged mice (FIG. 4B a&b). Similar observations were made with mice pre-treated once with BPZE1 (FIG. 4B c). However, two doses of BPZE1 markedly reduced ear swelling and inflammation, with reduced edema and cellular infiltration compared to the non BPZE1-treated animals (FIG. 4B d).

Example 6

Figure 5:
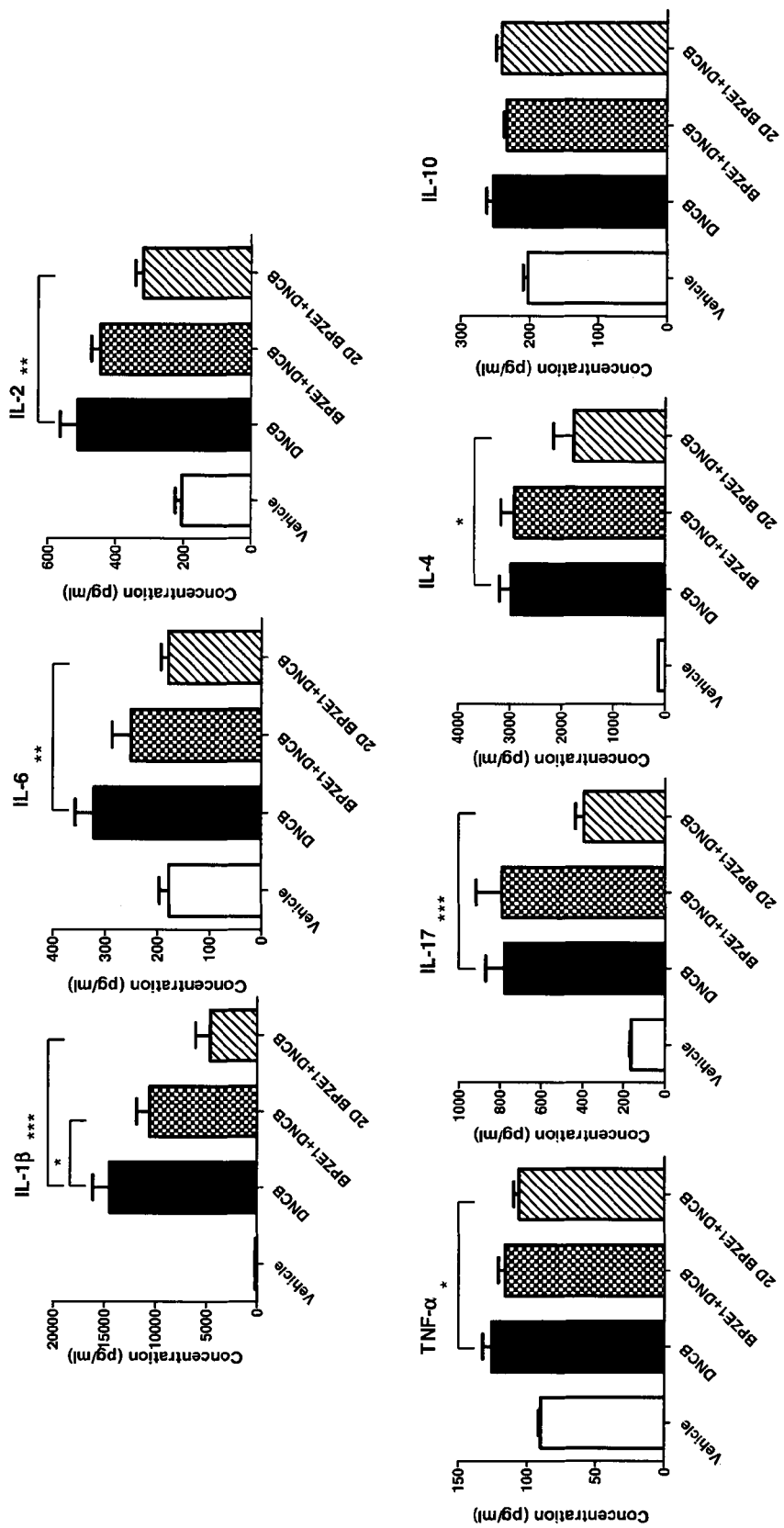
FIG. 5. Effects of BPZE1 pre-treatment on local cytokine production in the DNCB-induced CHS model. Two days after DNCB or vehicle challenge, ears from BPZE1 pre-treated or untreated mice were collected and homogenized, and cytokines production were determined in the individual homogenates by multiplex assay (n=5 mice per group). Values shown are the mean±SEM. * $P \leq 0.05$,  $P \leq 0.01$, * $P \leq 0.001$.

BPZE1 Pre-Treatment Down-Regulates the Production of Pro-Inflammatory Cytokines Induced by DNCB Examination of the cytokine profile in the ear homogenates from the different mouse groups showed that DNCB challenge triggered a marked increase in pro-inflammatory cytokines IL-1β, IL-2, IL-17, IL-6, TNF-α, and IL-4 (FIG. 5). Consistent with the reduced inflammation and edema observed by histology (FIG. 4B), 2 doses of BPZE1 resulted in significantly reduced levels of all the pro-inflammatory cytokines measured (FIG. 5). In contrast, the levels of IL-10 remained unchanged for all the groups (FIG. 5).

Example 7

BPZE1 Pre-Treatment does not Affect the Sensitization Phase

Figure 6:
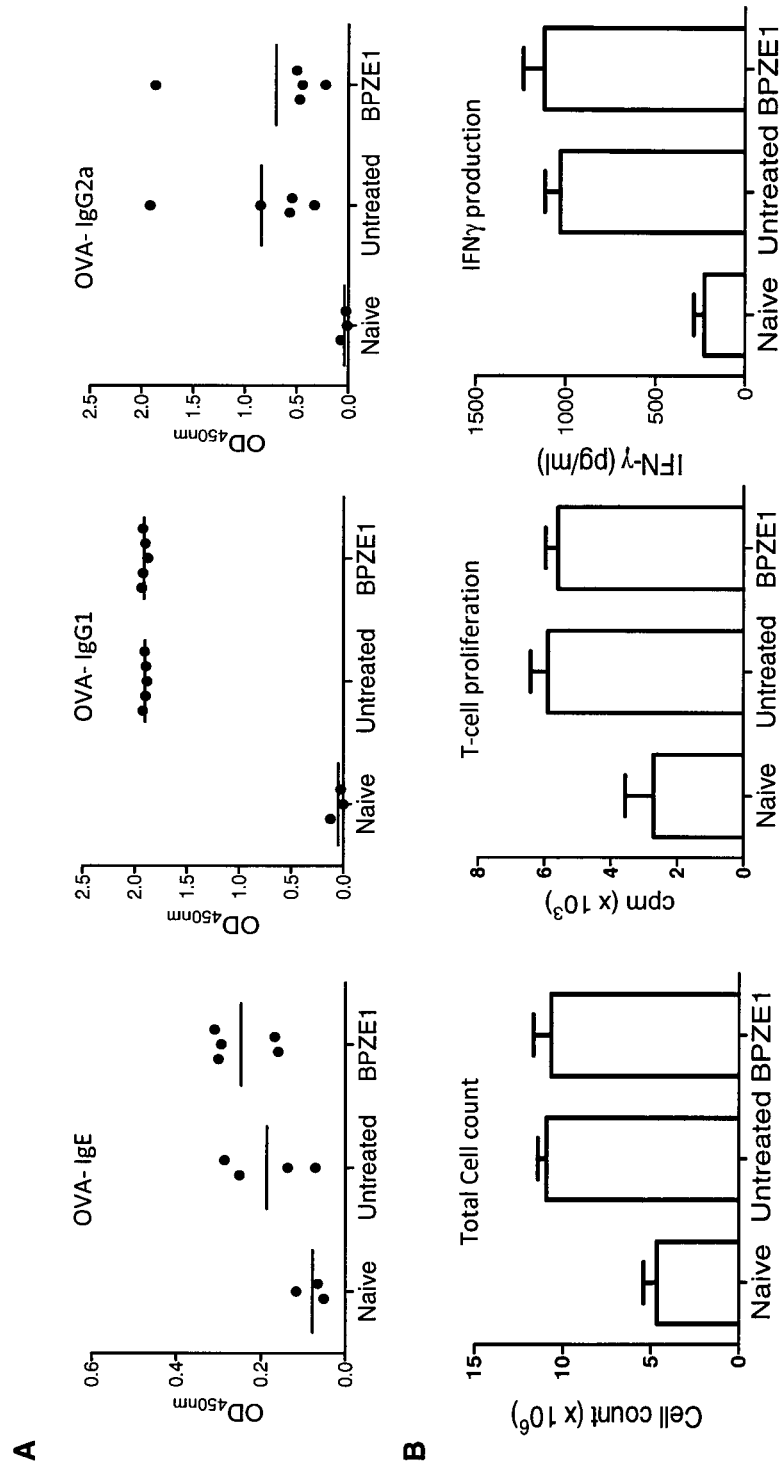
FIG. 6. Effect of BPZE1 pre-treatment on the sensitization phase. A) Mice were nasally pre-treated with BPZE1 (1 dose) or left untreated and OVA sensitized. Serum from naïve (n=3), untreated (n=4) and BPZE1-treated (n=4) groups was collected 1 week post-sensitization. The levels of OVA-specific IgE, IgG1, and IgG2a were determined by ELISA on individual sera diluted 1/5 (A) or 1/100 (B-C). B) Mouse groups (n=5) were nasally pre-treated with BPZE1 (2 doses) or left untreated and subjected to DNCB sensitization. Their auricular LNs were harvested 3 days post-sensitization for total cell count, T-cell proliferation upon re-stimulation with anti-CD3/CD28 antibodies, and IFNγ production in the culture supernatants as indicated. Each individual sample was assayed in triplicates.

To test whether BPZE1 pre-treatment affects the sensitization phase in both inflammation models, BPZE1 pre-treated or untreated mice were subjected to OVA or DNCB sensitization. One week post-OVA sensitization, the OVA-specific antibody responses were measured and comparable levels of OVA-specific IgE and IgG levels were observed in both BPZE1 pre-treated and untreated animals (FIG. 6). Similarly, 3 days post-DNCB sensitization, the auricular lymph nodes were harvested and the total cell counts, T-cell proliferation and IFNγ production upon in vitro re-stimulation were found comparable in both BPZE1 pre-treated and untreated animal groups (FIG. 6). Therefore, these results strongly support that BPZE1 pre-treatment does not affect the sensitization phase but instead impact on the effector cells that are recruited upon challenge.

Thus, prior BPZE1 nasal treatment suppressed OVA-induced lung inflammation and inflammatory cell recruitment, and significantly reduced IgE levels and cytokine production. Similarly, BPZE1 nasal pre-treatment markedly inhibited ear swelling, skin inflammation and production of pro-inflammatory cytokines in the DNCB-induced CHS model. For both models, it was shown that BPZE1 pre-treatment does not affect the sensitization phase. Upon challenge, BPZE1 pre-treatment selectively reduced the level of cytokines whose production is increased, and did not affect the basal level of other cytokines. Together these observations suggest that BPZE1 pre-treatment specifically targets those cytokine-producing effector cells that are recruited and involved in the inflammatory reaction.

This study demonstrates the broad anti-inflammatory properties of the attenuated *B. pertussis* BPZE1 strain in the context of allergic diseases.

All publications, patents, and patent applications cited in this specification are herein incorporated by reference in their entirety for all purposes as if each individual publication or patent application were specifically and individually indicated to be incorporated by reference for all purposes.

Although the foregoing aspects of the invention have been described in some detail by way of illustration and example for purposes of clarity of understanding, it will be readily apparent to one of ordinary skill in the art in light of the teachings that certain changes and modifications can be made thereto without departing from the spirit or scope of the appended claims.

REFERENCES

1. Li R, Lim A, Phoon M C, Narasaraju T, Ng J K, Poh W P, et al. Attenuated *Bordetella pertussis* protects against highly pathogenic influenza A viruses by dampening the cytokine storm. J Virol 2010; 84(14):7105-13.
2. Galli S J, Tsai M, Piliponsky A M. The development of allergic inflammation. Nature 2008; 454(7203):445-54.
3. Masoli M, Fabian D, Holt S, Beasley R. The global burden of asthma: executive summary of the GINA Dissemination Committee report. Allergy 2004; 59(5):469-78.
4. Kim H Y, DeKruyff R H, Umetsu D T. The many paths to asthma: phenotype shaped by innate and adaptive immunity. Nat Immunol 2010; 11(7):577-84.
5. Novak N, Simon D. Atopic dermatitis—from new pathophysiologic insights to individualized therapy. Allergy 2011; 66:830-9.
6. Watanabe H, Unger M, Tuvel B, Wang B, Sauder D N. Contact hypersensitivity: the mechanism of immune responses and T cell balance. J Interferon Cytokine Res 2002; 22(4):407-12.
7. Saint-Mezard P, Berard F, Dubois B, Kaiserlian D, Nicolas J F. The role of CD4+ and CD8+ T cells in contact hypersensitivity and allergic contact dermatitis. Eur J Dermatol 2004; 14(3):131-8.
8. Strachan D P. Family size, infection and atopy: the first decade of the "hygiene hypothesis". Thorax 2000; 55 Suppl 1:S2-10.
9. Ennis D P, Cassidy J P, Mahon B P. Prior *Bordetella pertussis* infection modulates allergen priming and the severity of airway pathology in a murine model of allergic asthma. Clin Exp Allergy 2004; 34(9):1488-97.

10. Papadopoulos N G, Christodoulou I, Rohde G, Agache I, Almqvist C, Bruno A, et al. Viruses and bacteria in acute asthma exacerbations—A GA²LEN-DARE systematic review. Allergy 2011; 66:458-68.
11. Lukacs N R, Tekkanat K K, Berlin A, Hogaboam C M, Miller A, Evanoff H, et al. Respiratory syncytial virus predisposes mice to augmented allergic airway responses via IL-13-mediated mechanisms. J Immunol 2001; 167(2): 1060-5.
12. Kavanagh H, Noone C, Cahill E, English K, Locht C, Mahon B P. Attenuated *Bordetella pertussis* vaccine strain BPZE1 modulates allergen-induced immunity and prevents allergic pulmonary pathology in a murine model. Clin Exp Allergy 2010.
13. Fischer K, Stein K, Ulmer A J, Lindner B, Heine H, Hoist O. Cytokine-inducing lipoteichoic acids of the allergy-protective bacterium *Lactococcus lactis* G 121 do not activate via Toll-like receptor 2. Glycobiology 2011.
14. Bieber T, Simon H-U. Allergen-specific immunotherapy: current concepts and future directions. Allergy 2011; 66:709-12.
15. Mielcarek N, Debrie A S, Raze D, Bertout J, Rouanet C, Younes A B, et al. Live attenuated *B. pertussis* as a single-dose nasal vaccine against whooping cough. PLoS Pathog 2006; 2(7):e65.
16. Menozzi F D, Mutombo R, Renauld G, Gantiez C, Hannah J H, Leininger E, et al. Heparin-inhibitable lectin activity of the filamentous hemagglutinin adhesin of *Bordetella pertussis*. Infect Immun 1994; 62(3):769-78.
17. Bao Z, Lim S, Liao W, Lin Y, Thiemermann C, Leung B P, et al. Glycogen synthase kinase-3beta inhibition attenuates asthma in mice. Am J Respir Crit. Care Med 2007; 176(5): 431-8.
18. Duan W, Chan J H, Wong C H, Leung B P, Wong W S. Anti-inflammatory effects of mitogen-activated protein kinase kinase inhibitor U0126 in an asthma mouse model. J Immunol 2004; 172(11):7053-9.
19. Evans C M, Williams O W, Tuvim M J, Nigam R, Mixides G P, Blackburn M R, et al. Mucin is produced by clara cells in the proximal airways of antigen-challenged mice. Am J Respir Cell Mol Biol 2004; 31(4):382-94.
20. Ennis D P, Cassidy J P, Mahon B P. Whole-cell pertussis vaccine protects against *Bordetella pertussis* exacerbation of allergic asthma. Immunol Lett 2005; 97(1):91-100.
21. Ennis D P, Cassidy J P, Mahon B P. Acellular pertussis vaccine protects against exacerbation of allergic asthma due to *Bordetella pertussis* in a murine model. Clin Diagn Lab Immunol 2005; 12(3):409-17.
22. Feunou P F, Ismaili J, Debrie A S, Huot L, Hot D, Raze D, et al. Genetic stability of the live attenuated *Bordetella pertussis* vaccine candidate BPZE1. Vaccine 2008; 26(45): 5722-7.
23. Skerry C M, Cassidy J P, English K, Feunou-Feunou P, Locht C, Mahon B P. A live attenuated *Bordetella pertussis* candidate vaccine does not cause disseminating infection in gamma interferon receptor knockout mice. Clin Vaccine Immunol 2009; 16(9):1344-51.
24. Bao Z, Guan S, Cheng C, Wu S, Wong S H, Kemeny D M, et al. A novel antiinflammatory role for andrographolide in asthma via inhibition of the nuclear factor-kappaB pathway. Am J Respir Crit. Care Med 2009; 179(8):657-65.
25. Guan S P, Kong L R, Cheng C, Lim J C, Wong W S. Protective role of 14-deoxy-11,12-didehydroandrographolide, a noncytotoxic analogue of andrographolide, in allergic airway inflammation. J Nat Prod 2011; 74(6):1484-90.
26. Nahori M A, Lagranderie M, Lefort J, Thouron F, Joseph D, Winter N, et al. Effects of *Mycobacterium bovis* BCG on the development of allergic inflammation and bronchial hyperresponsiveness in hyper-IgE BP2 mice vaccinated as newborns. Vaccine 2001; 19(11-12):1484-95.
27. Page K R, Scott A L, Manabe Y C. The expanding realm of heterologous immunity: friend or foe? Cell Microbiol 2006; 8(2):185-96.
28. Walzl G, Tafuro S, Moss P, Openshaw P J, Hussell T. Influenza virus lung infection protects from respiratory syncytial virus-induced immunopathology. J Exp Med 2000; 192(9):1317-26.
29. Tsitoura D C, Kim S, Dabbagh K, Berry G, Lewis D B, Umetsu D T. Respiratory infection with influenza A virus interferes with the induction of tolerance to aeroallergens. J Immunol 2000; 165(6):3484-91.
30. Hogan R J, Zhong W, Usherwood E J, Cookenham T, Roberts A D, Woodland D L. Protection from respiratory virus infections can be mediated by antigen-specific CD4 (+) T cells that persist in the lungs. J Exp Med 2001; 193(8):981-6.
31. de Bree G J, van Leeuwen E M, Out T A, Jansen H M, Jonkers R E, van Lier R A. Selective accumulation of differentiated CD8+ T cells specific for respiratory viruses in the human lung. J Exp Med 2005; 202(10):1433-42.
32. Dahl M E, Dabbagh K, Liggitt D, Kim S, Lewis D B. Viral-induced T helper type 1 responses enhance allergic disease by effects on lung dendritic cells. Nat Immunol 2004; 5 (3):337-43.
33. Beyer M, Bartz H, Horner K, Doths S, Koerner-Rettberg C, Schwarze J. Sustained increases in numbers of pulmonary dendritic cells after respiratory syncytial virus infection. J Allergy Clin Immunol 2004; 113(1):127-33.
34. Didierlaurent A, Goulding J, Patel S, Snelgrove R, Low L, Bebien M, et al. Sustained desensitization to bacterial Toll-like receptor ligands after resolution of respiratory influenza infection. J Exp Med 2008; 205(2):323-9.

The invention claimed is:

1. A method of reducing a T-lymphocyte helper type 1 (Th1)-dominated allergic reaction in a mammal, comprising: colonizing the respiratory tract of the mammal by intranasally administering a live mutated *Bordetella pertussis* strain to the mammal, wherein the strain is mutated to reduce its production of functional *pertussis* toxin, dermonecrotic toxin, and tracheal cytotoxin while retaining the ability to colonize the mammal, wherein the colonization of the mammal elicits an anti-inflammatory response which reduces the Th1-dominated allergic reaction in the mammal.

2. The method of claim 1, wherein the strain comprises a mutated pertussis toxin (ptx) gene, a deleted or mutated dermonecrotic (dnt) gene, and a heterologous ampG gene.

3. The method of claim 1, wherein the *Bordetella pertussis* strain is administered prior to onset of the allergic reaction in the mammal.

4. The method of claim 2, wherein the heterologous ampG gene is an *E. coli* ampG gene that replaces the wild-type *Bordetella* strain ampG gene.

5. The method of claim 2, wherein the mutation of the ptx gene comprises the substitution of an amino acid involved in substrate binding and/or an amino acid involved in catalysis.

6. The method of claim 5, wherein the substitution of the amino acid involved in substrate binding comprises R9K and the substitution of the amino acid involved in catalysis comprises E129G.

7. The method of claim 2, wherein the heterologous ampG gene is the only heterologous gene in the strain.

8. The method of claim 1, wherein the Th1-dominated allergic reaction is contact dermatitis.

* * * * *